United States Patent [19]
Navab

[11] Patent Number: 6,028,912
[45] Date of Patent: Feb. 22, 2000

[54] APPARATUS AND METHOD FOR POINT RECONSTRUCTION AND METRIC MEASUREMENT ON RADIOGRAPHIC IMAGES

[75] Inventor: Nassir Navab, Erlangen, Germany

[73] Assignee: Siemens Corporate Research, Inc., Princeton, N.J.

[21] Appl. No.: 08/940,925

[22] Filed: Sep. 30, 1997

[51] Int. Cl.[7] .................................................. G01N 23/04
[52] U.S. Cl. ........................... 378/62; 378/98.5; 378/98.2
[58] Field of Search .......................... 378/62, 98.2, 98.5; 600/424

[56] References Cited

U.S. PATENT DOCUMENTS

| | | | |
|---|---|---|---|
| 3,991,310 | 11/1976 | Morrison | 378/65 |
| 4,608,977 | 9/1986 | Brown | 606/130 |
| 4,638,798 | 1/1987 | Shelden et al. | 606/130 |
| 4,722,336 | 2/1988 | Kim et al. | 606/130 |
| 4,750,487 | 6/1988 | Zanetti | 128/303 B |
| 4,823,306 | 4/1989 | Barbic et al. | 364/900 |
| 4,883,053 | 11/1989 | Simon | 606/130 |
| 4,930,525 | 6/1990 | Palestrant | 128/898 |
| 4,979,815 | 12/1990 | Tsikos | 356/1 |
| 5,154,723 | 10/1992 | Kubota et al. | 606/130 |
| 5,189,690 | 2/1993 | Samuel | 378/162 |
| 5,201,742 | 4/1993 | Hasson | 606/130 |
| 5,219,351 | 6/1993 | Teubner et al. | 606/130 |
| 5,221,283 | 6/1993 | Chang | 606/130 |
| 5,330,485 | 7/1994 | Clayman et al. | 606/130 |
| 5,368,015 | 11/1994 | Wilk | 128/4 |
| 5,387,220 | 2/1995 | Pisharodi | 606/130 |
| 5,389,101 | 2/1995 | Heilbrun et al. | 606/130 |
| 5,398,684 | 3/1995 | Hardy | 606/130 |
| 5,474,564 | 12/1995 | Clayman et al. | 606/130 |
| 5,584,292 | 12/1996 | Cheung | 128/653.1 |
| 5,609,152 | 3/1997 | Pellegrino et al. | 128/653.1 |
| 5,618,288 | 4/1997 | Calvo | 606/130 |
| 5,628,327 | 5/1997 | Unger et al. | 128/749 |
| 5,638,819 | 6/1997 | Manwaring et al. | 600/424 |
| 5,647,373 | 7/1997 | Paltieli | 128/749 |

FOREIGN PATENT DOCUMENTS

WO 91/07922 of 0000 WIPO.

*Primary Examiner*—David P. Porta
*Assistant Examiner*—David Vernon Bruce
*Attorney, Agent, or Firm*—Adel A. Ahmed

[57] ABSTRACT

A method for point reconstruction and metric measurement on radiographic images comprises the following steps: positioning a fluoroscope for producing a fluoroscopic image, in a position where an operator, such as a physician, can observe points inside a patient's body on which points at least one of reconstruction and metric measurement are to be carried out; positioning a positioning device on the patient's body at an arbitrarily selected point F visible in a radiographic image, designating target points $T^i$, being points to be reconstructed, by the operator on the radiographic image; finding planes $\pi^i$ passing through the X-ray source and a line $FT^i$ as describe in the step I and II in the invention disclosure; rotating the fluoroscope to a new position and taking a new radiographic image from this new viewpoint, designating target points $T^i$, being points to be reconstructed, by the operator the physician on the new radiographic image; computing first the orientation of vectors $Ft^i$; computing the length of vectors $\|FT^i\|$; visualizing points $\{T^i, i=1 \ldots n\}$ in a coordinate system associated to the point F; and computing distances $\|T^iT^j\|$, $i,j=1 \ldots n$.

19 Claims, 23 Drawing Sheets

APPARATUS AND METHOD FOR POINT RECONSTRUCTION AND METRIC MEASUREMENT ON RADIOGRAPHIC IMAGES

The present invention relates to an apparatus and a method for point reconstruction and metric measurement using a device actively guided by the visual feedback and, more particularly, point reconstruction and metric measurement on radiographic/fluoroscopic images such as X-ray images.

Needle biopsy is a frequently used type of surgical intervention. Typically, a fine needle is used to remove tissue portions from a lesion inside the body. If the lesion is very small and is deep-seated within the body or is not palpable, the surgeon needs guidance in order to make sure that the tip of the needle reaches the desired location. The surgeon may also desire to know the distance between the target and another anatomical structure in order to plan the intervention accurately, and reduce risks associated with the intervention.

An object of the present invention is generally to perform 3D reconstruction of target points inside the patient body from radiographic images and to compute the metric distances between these target points. This object is also applicable to the field of needle biopsy applications. The invention is preferably practiced in conjunction with apparatus and components disclosed in a copending patent application, APPARATUS AND METHOD FOR DETERMINING THE CORRECT INSERTION DEPTH FOR A BIOPSY NEEDLE, in the names of Navab and Geiger, filed Sep. 30, 1996, and accorded Ser. No. 08/722,708 and whereof the subject matter will be discussed in detail below as part of the environment in which the present invention is illustratively practiced, though it is by no means limited to this environment and application. Thus, the present invention is likewise applicable to diagnostic purposes and to fields such performing investigations and planning for surgery.

In the following, apparatus and method in accordance with the present invention are described. It is emphasized that the present invention is not limited in its application to needle biopsy. The present invention facilitates 3D reconstruction and metric measurements even with the use of an inexpensive X-ray fluoroscopy device, and can also be used, for example, in surgical planning or for diagnostic purposes. In a described embodiment a previously disclosed automatic positioning device is utilized as disclosed in the aforementioned patent application of Navab et al., with a minimum user interaction with the screen of a fluoroscope or the like display instrument in order to define the points to be reconstructed or the points for which metric distances in space need to be measured.

Currently used image based guidance methods include the following. Ultrasound (US), X-ray fluoroscopy, CT fluoroscopy, and CT/MRI in combination with real time registration tools. The first three methods provide real time intra-operative images of the patient and enable the surgeon to see the needle as it approaches the target. Ultrasound is relatively inexpensive and is a readily available image modality. However, its usage for guidance is limited to lesions that are close to the skin and that show a well defined signal.

The X-ray fluoroscope is a widely available, low cost two-dimensional (2D) imaging equipment. Since it shows a two-dimensional projection, two (generally orthogonal) views are necessary in order to determine the biopsy needle position. This can be done by turning the arm of a simple fluoroscope, such as a C-arm fluoroscope, an example of which is shown in FIG. 1, or by using a fluoroscope such as that illustrated in FIG. 2 that provides two simultaneous orthogonal views. Since the needle has to be manipulated in the image field, one cannot avoid an X-ray exposure of the physician when using such techniques. As is well-known, unnecessary exposure of health workers to X-ray radiation is undesirable in that it is generally believed that excessive exposure to such radiation is associated with hazards to health and it is therefore desirable that exposure should be avoided to the extent possible.

CT-Fluoroscopy permits real-time display of CT images. The physician controls X-ray exposure during continuous tube rotation. The exact position of the needle can be traced by moving the table. In the case for CT-Fluoroscopy also, the surgeon is exposed to X-rays.

CT/MRI in combination with real time registration tools is based on pre-operative 3-D data acquisition (CT or MRI). The lesion is outlined in the resulting dataset. During the actual biopsy, the position and orientation of the patient and the needle have to be known precisely and aligned with the pre-operative data.

Therefore two registrations have to be used for guiding the needle: the pre-operative data showing the lesion has to be registered with the patient. This can be done by attaching invariant markers to the patient (stereo-tactic frames) before data acquisition or by matching invariant patient features, such as the skull or bones.

The needle has to be registered with the patient. One possibility is to attach optical markers to the needle which can be tracked by a system of cameras or by X-ray fluoroscopy, or to use mechanical devices like passive robot arms that register the position of the needle at any moment. This technique requires highly specialized and costly 3-D imaging facilities that are typically only available at a few research sites. Despite the image guidance, a successful biopsy procedure still depends on the manual skills and judgement of the surgeon who is manipulating the needle.

There is a need for an alignment device that is adjustable to the right direction and that indicates the distance to a deep-seated target. Among the benefits that result from such a device are acceleration of the procedure, increase of the safety of the procedure, and reduction of radiation exposure for both the patient and for the surgeon.

Prior applications for U.S. Letters Patent in which the present inventor is a named inventor are of particular interest as background to the present application. The patent applications, whereof the disclosure is herein incorporated by reference to the extent not inconsistent with the present invention, are as follows.

CALIBRATION APPARATUS FOR X-RAY GEOMETRY, in the names of Navab and Bani-Hashemi, filed Dec. 21, 1995, and accorded Ser. No. 08/576,736 now U.S. Pat. No. 5,835,563;

CALIBRATION SYSTEM AND METHOD FOR X-RAY GEOMETRY, in the names of Nabab and Bani-Hashemi, filed Dec. 21, 1995, and accorded Ser. No. 08/576,718 now U.S. Pat. No. 5,822,396;

APPARATUS AND METHOD FOR POSITIONING A BIOPSY NEEDLE, in the names of Navab and Geiger, filed Sep. 30, 1996, and accorded Ser. No. 08/722,725;

APPARATUS AND METHOD FOR POSITIONING A BIOPSY NEEDLE, in the names of Navab and Geiger, filed Sep. 30, 1996, and accorded Ser. No. 08/722,707;

APPARATUS AND METHOD FOR DETERMINING THE CORRECT INSERTION DEPTH FOR A BIOPSY NEEDLE, in the names of Navab and Geiger, filed Sep.

30, 1996, and accorded Ser. No. 08/722,708, herein above referred to; and

TRIGONOMETRIC DEPTH GAUGE FOR BIOPSY NEEDLE, in the name of Geiger and Navab, and accorded Ser. No. 08/722,724, filed Sep. 30, 1996.

Drawings of the aforelisted patent applications are helpful to a fuller understanding of the present invention and are herein included to help illustrate an example of the background and environment in which the present invention can be used.

In the aforementioned application for patent entitled APPARATUS AND METHOD FOR DETERMINING THE CORRECT INSERTION DEPTH FOR A BIOPSY NEEDLE, there is described an apparatus for determining a proper insertion depth of a biopsy needle to be inserted at a selected point on the body of a patient so that a sampling end of the needle just reaches to a designated target area within the body. Briefly, the apparatus disclosed in the above-mentioned patent application to Navab et al., comprises at least one straight calibrated pointing device aligned to point through the selected point in a straight line passing through the designated target region, the pointing device exhibiting first and second markers along its length such that respective images are formed on a first image plane by utilizing radiation from a radiation source, along with images corresponding to the selected point and the target area, the images being formed along a straight line in this order: (A) the first marker, (B) the second marker, (C) the selected point, and (D) the target region. The apparatus includes an arrangement for measuring distances on the image plane between images (A), (B), (C), and (D); and a calculator for calculating the cross ratio of the distances, whereby the proper insertion depth of the biopsy needle is determined. The disclosure of the above application is hereby incorporated by reference as background information for the present application to the extent it is not inconsistent therewith.

In performing the method, it is frequently important for the surgical practitioner to be able to obtain a correct measurement reading of the length of a blood vessel. It is also important in many circumstances to obtain a measurement of the distance of an anatomical part, such as a blood vessel, from another anatomical part or feature. Furthermore, such measurements are needed to be performed in real time during a medical procedure and should be simple and make the measurement result quickly available.

While fluoroscopic images have been in use by medical practitioners for many years, metric measurements were not practicable. Expensive and time-consuming tomographic reconstruction of the whole volume in the view is likewise not a desirable solution to the problem.

In accordance with an aspect of the invention a method for point reconstruction and metric measurement on radiographic images comprises the following steps: positioning a fluoroscope for producing a fluoroscopic image, in a position where an operator, such as a physician, can observe points inside a patient's body on which points at least one of reconstruction and metric measurement are to be carried out; positioning a positioning device on the patient's body at an arbitrarily selected point F visible in a radiographic image, designating target points $T^i$, being points to be reconstructed, by the operator on the radiographic image; finding planes $\pi^i$ passing through the X-ray source and a line $FT^i$ as described in steps I and II described hereinafter; rotating the fluoroscope to a new position and taking a new radiographic image from this new viewpoint, designating target points $T^i$, being points to be reconstructed, by the operator of the physician on the new radiographic image; computing first the orientation of vectors $Ft^i$; computing the length of vectors $\|FT^i\|$; visualizing points $\{T^i, i=1 \ldots n\}$ in a coordinate system associated to the point F; and computing distances $\|T^iT^j\|$, $i,j=1 \ldots n$.

In accordance with an aspect of the invention a method for point reconstruction and metric measurement on radiographic images the step of designating target points $T^i$ is performed on the radiographic image by using a mouse coordinate translator.

In accordance with an aspect of the invention apparatus for point reconstruction and metric comprises apparatus for positioning a fluoroscope for producing a fluoroscopic image, in a position where an operator, such as a physician, can observe points inside a patient's body on which points at least one of reconstruction and metric measurement are to be carried out; apparatus for positioning a positioning device on the patient's body at an arbitrarily selected point F visible in a radiographic image, apparatus for designating target points $T^i$, being points to be reconstructed, by the operator on the radiographic image; apparatus for finding planes $\pi^i$ passing through the X-ray source and a line $FT^i$ as describe in the step I and II in the invention disclosure; apparatus for rotating the fluoroscope to a new position and taking a new radiographic image from this new viewpoint, apparatus for designating target points $T^i$, being points to be reconstructed, by the operator the physician on the new radiographic image; apparatus for computing first the orientation of vectors $Ft^i$; apparatus for computing the length of vectors $\|FT^i\|$; apparatus for visualizing points $\{T^i, i=1 \ldots n\}$ in a coordinate system associated to the point F; and apparatus for computing distances $\|T^iT^j\|$, $i,j=1 \ldots n$.

In accordance with another aspect of the invention, apparatus for point reconstruction and metric measurement on radiographic images in an X-ray system including an X-ray source comprises: apparatus for positioning the X-ray system such that deep seated targets $T^i$ are visible on a fluoroscopy image; apparatus for positioning positioning device at an arbitrary point F close to a patient's body and so as to be visible in the last-mentioned fluoroscopy image; apparatus for designating target points $T^i$, being points to be reconstructed, by an operator, such as a physician, on this last-mentioned fluoroscopy image; apparatus for adjusting the positioning device to an initial configuration defined by $[\theta=\theta_1, \phi=0, \alpha=0]$; apparatus for each target point $T^i$, moving the positioning needle around the point F until its image goes through the target image $t^i$; apparatus for saving positioning parameters $[\theta=\theta_1, \phi=\phi^i_1, \alpha=0]$ of the positioning device; apparatus for changing the positioning device to a new configuration defined by $[\theta=\theta_2=\theta_1, \phi=0, \alpha=0]$; apparatus for moving for each target point $T^i$, the positioning device around the point F until its image goes through the target image $t^i$; apparatus for saving positioning parameters $[\theta=\theta_2, \phi=\phi^i_2, \alpha=0]$ of the pointing device; apparatus for computing, for each target point $T^i$ using $(\theta_1, \phi^i_1, \theta_2, \phi^i_2)$, the quantity $\theta_i'$ and $\alpha_i'$, defining a plane passing through the X-ray source, F, and $T^i$; apparatus for moving the X-ray system to a different position, such as by rotating it by 90 degrees, such that the deep seated targets $T^i$ are visible on the radiographic image; apparatus for moving, for each target point, $T^i$, the positioning device around the point F until its image goes through the target image $t'^i$; apparatus for saving positioning parameters $[\theta=\theta_i', \phi=\phi_i', \alpha=\alpha_i']$ of the pointing device; and apparatus for computing the depth of the target.

In summary, the present invention relates to an apparatus and method for point reconstruction and metric measurement using a device actively guided by the visual feedback and, more particularly, point reconstruction and metric measurement on radiographic/fluoroscopic images using a previously proposed automatic positioning device and a minimum user interaction with the screen of a fluoroscope or the like display instrument in order to define the points to be reconstructed or the points for which metric distances in space need to be measured.

In summary in order to reconstruct a point seated deep inside the patient's body, the physician position positioning device in accordance with the invention defined in the aforementioned patent application by Navab et al.) on the patient body at an arbitrary point F preferably near to the points $T^i$ he wants to reconstruct or do metric distance measurement on. The positioning device finds the planes $\pi^i$ passing through the X-ray source and the line $FT^i$ as describe in the step I and II above. The physician is then asked to rotate the C-arm to a new position; the larger is the angle of rotation the more accurate is the resulting orientation of the line $FT^i$. From this new viewpoint the method described in accordance with the present invention computes first the orientation of the vector $FT^i$, and then the length of this vector $\|FT^i\|$, through the step III and IV described above. All target points $T^i$ are reconstructed since the point F is known to the device in accordance with the invention and the orientation and the length of all the vectors $FT^i$ are computed in the steps described above. Therefore the distances between all target points $T^i$ can be calculated and these points can be visualized in 3D with their correct relative positioning in space. This can help the physician in planning the intervention in many ways including making sure that he is far enough from some particular anatomical entities during the intervention.

The invention will be more fully understood from the detailed description of preferred embodiments, in conjunction with the drawing, not necessarily to scale, in which FIG. 1 shows a known type of C-arm fluoroscope, such as may be utilized in conjunction with the present invention;

Figure 4:
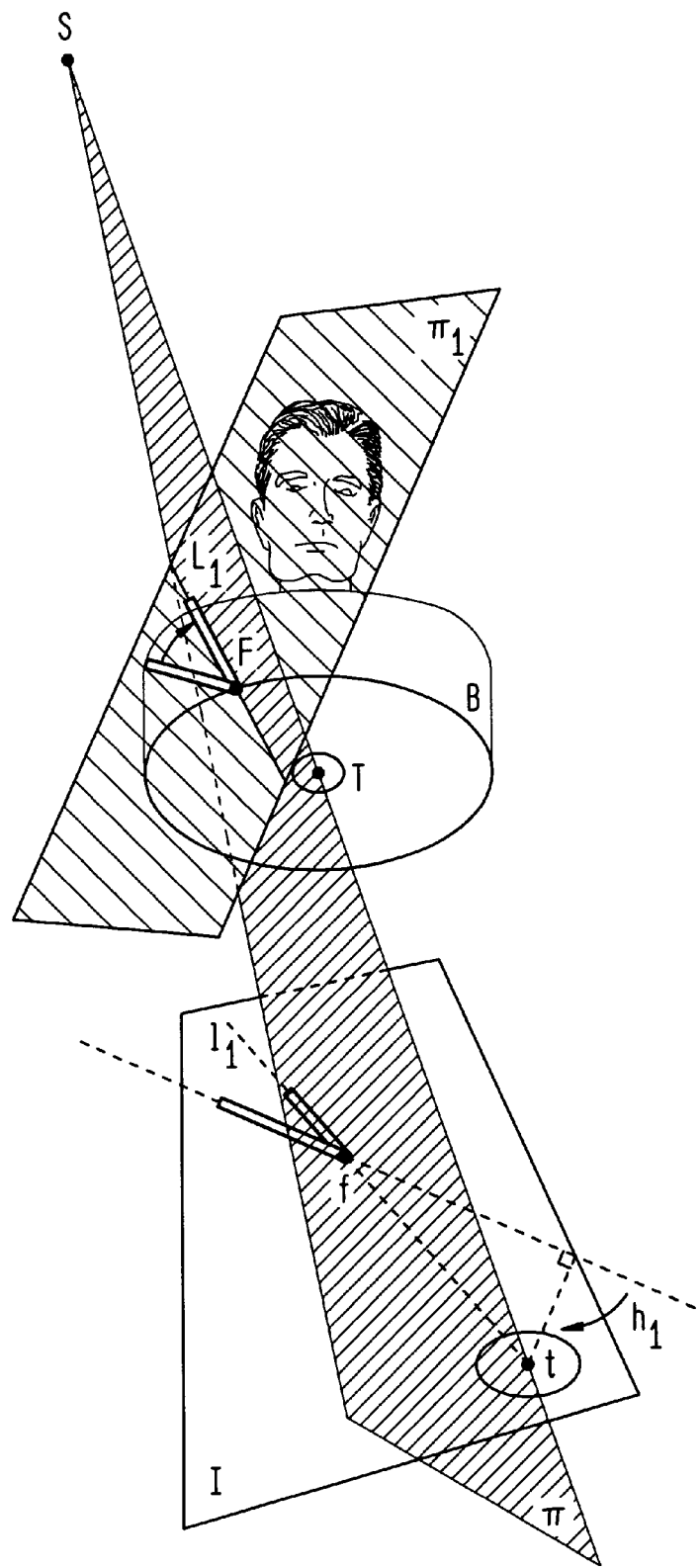
Figure 5:
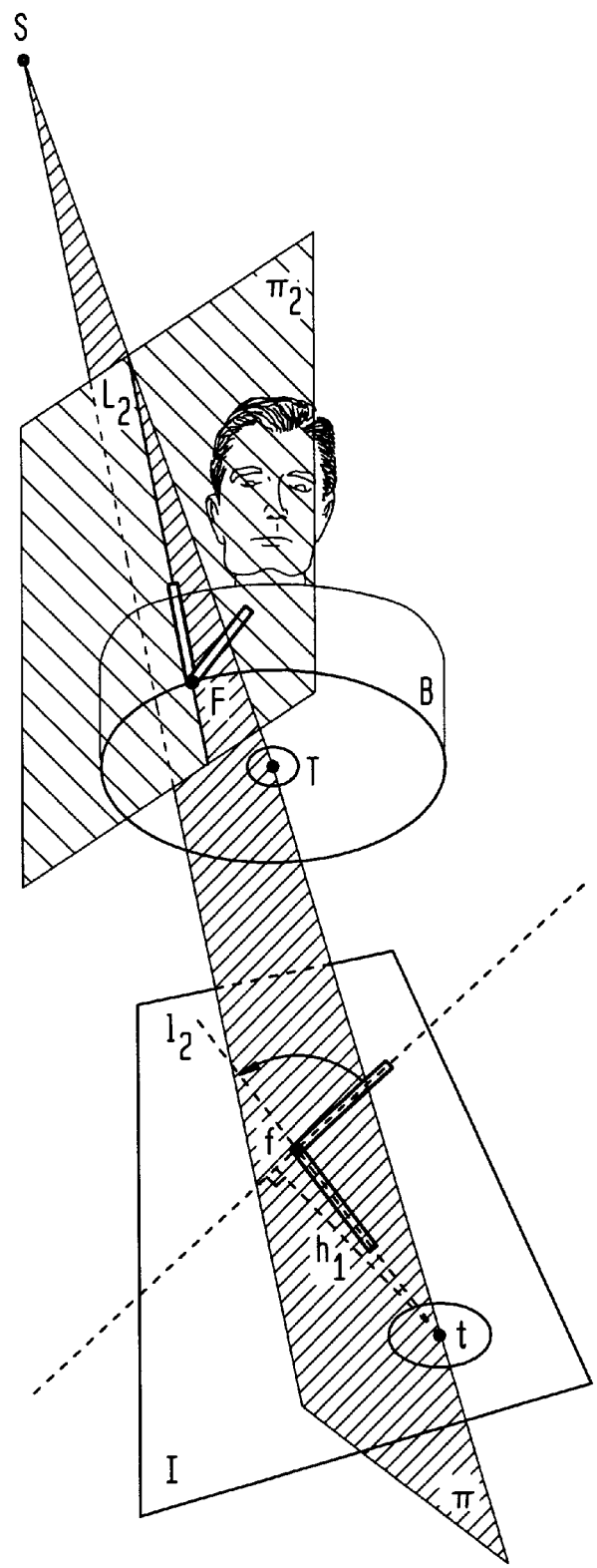
Figure 6:
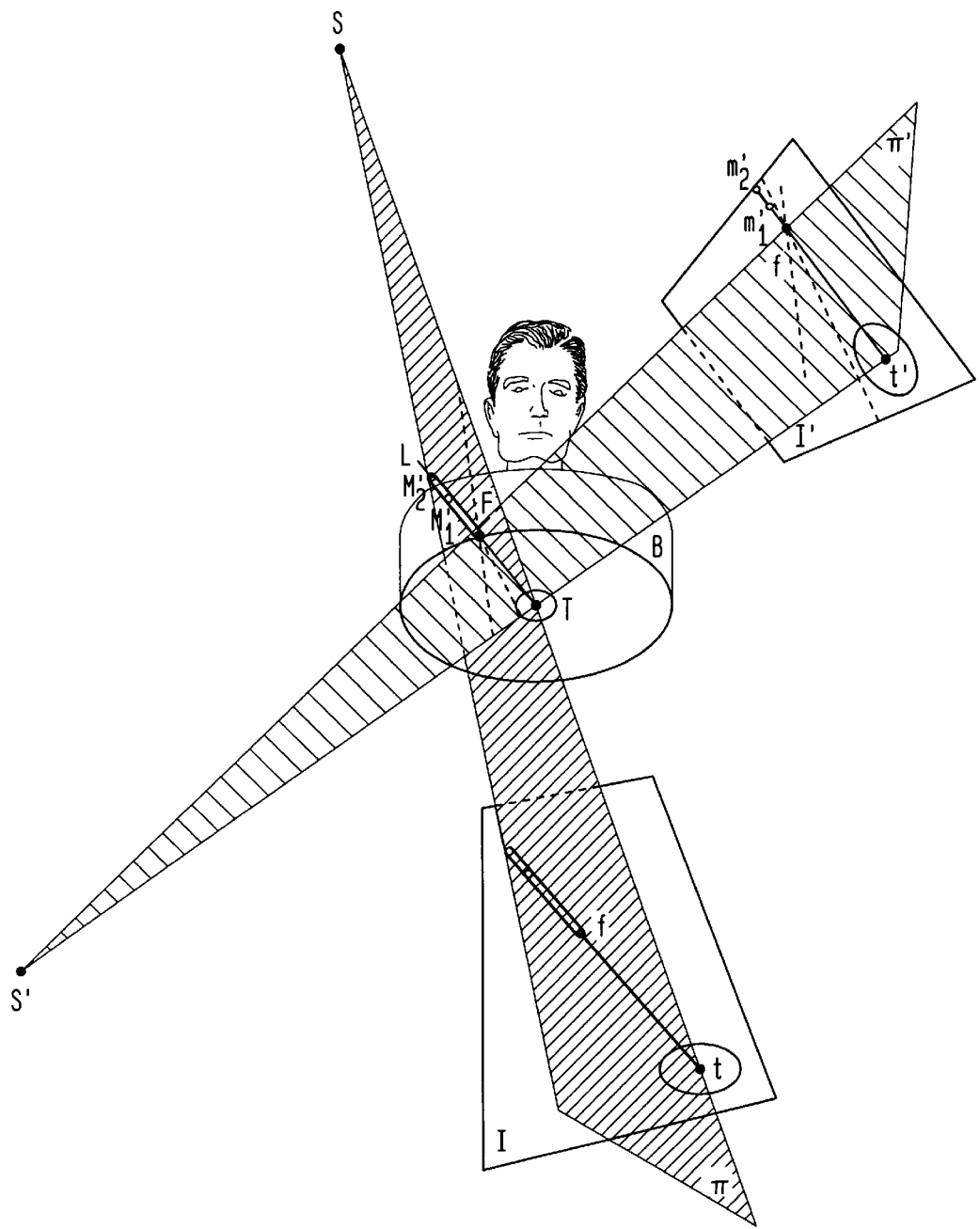
Figure 7:
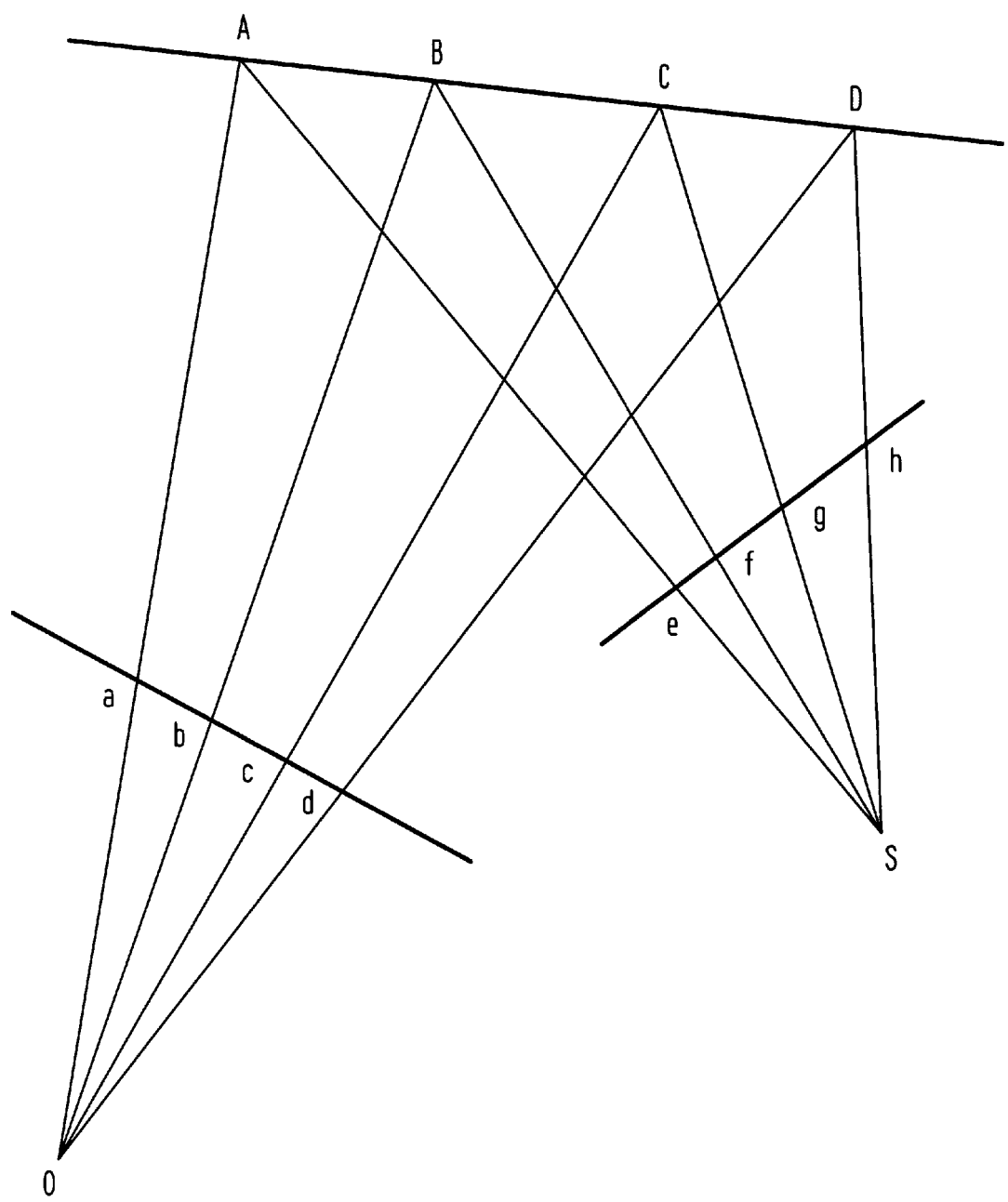
Figure 8:
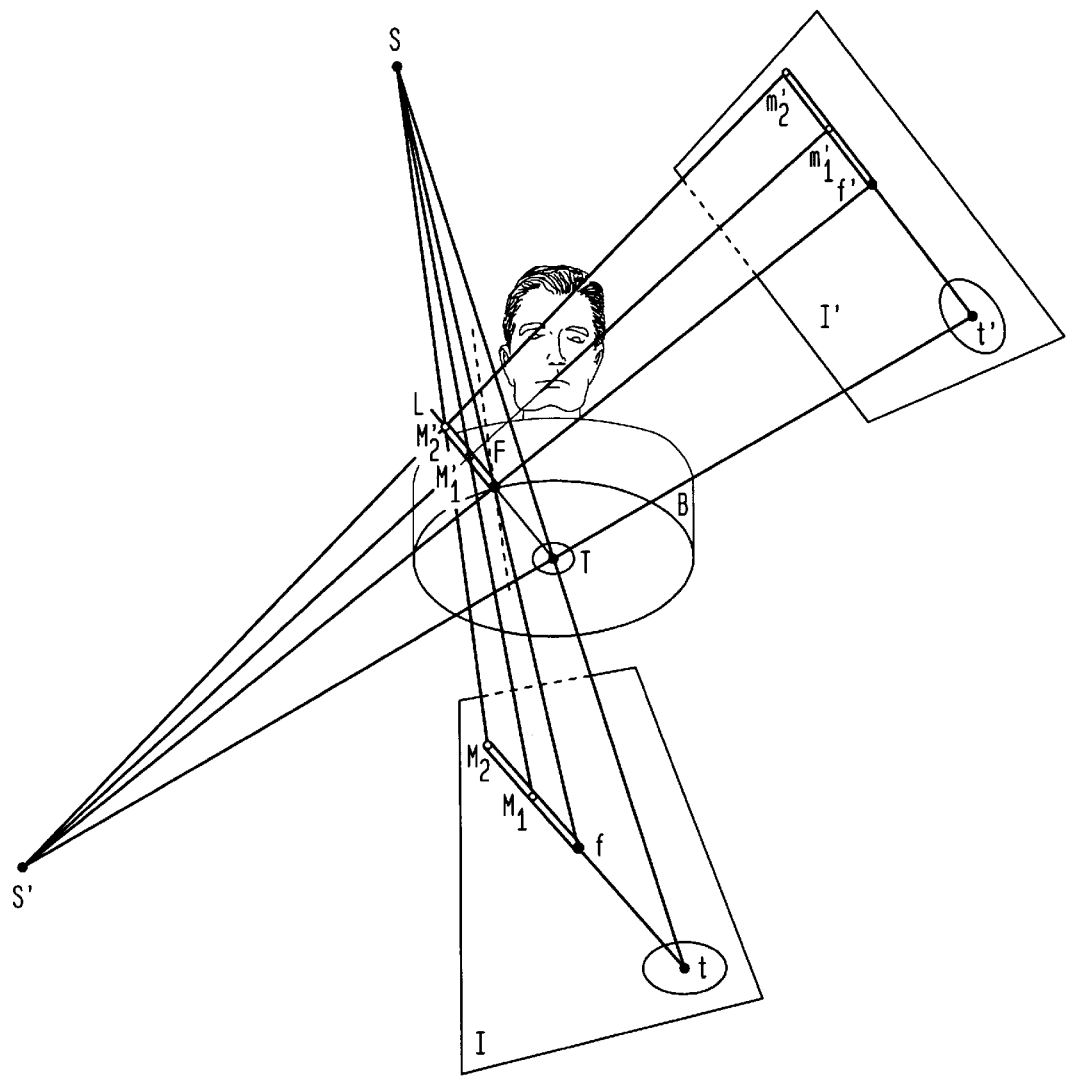
Figure 9:
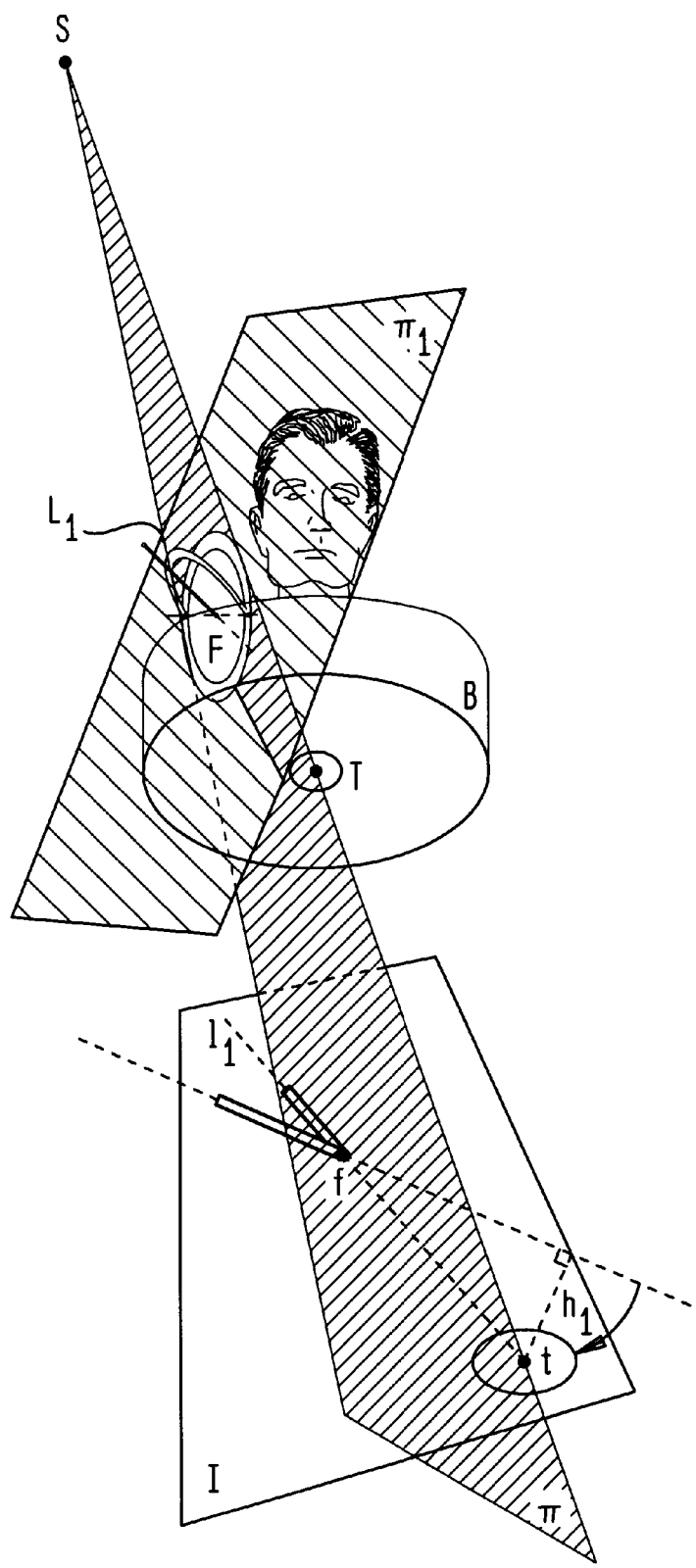
Figure 10:
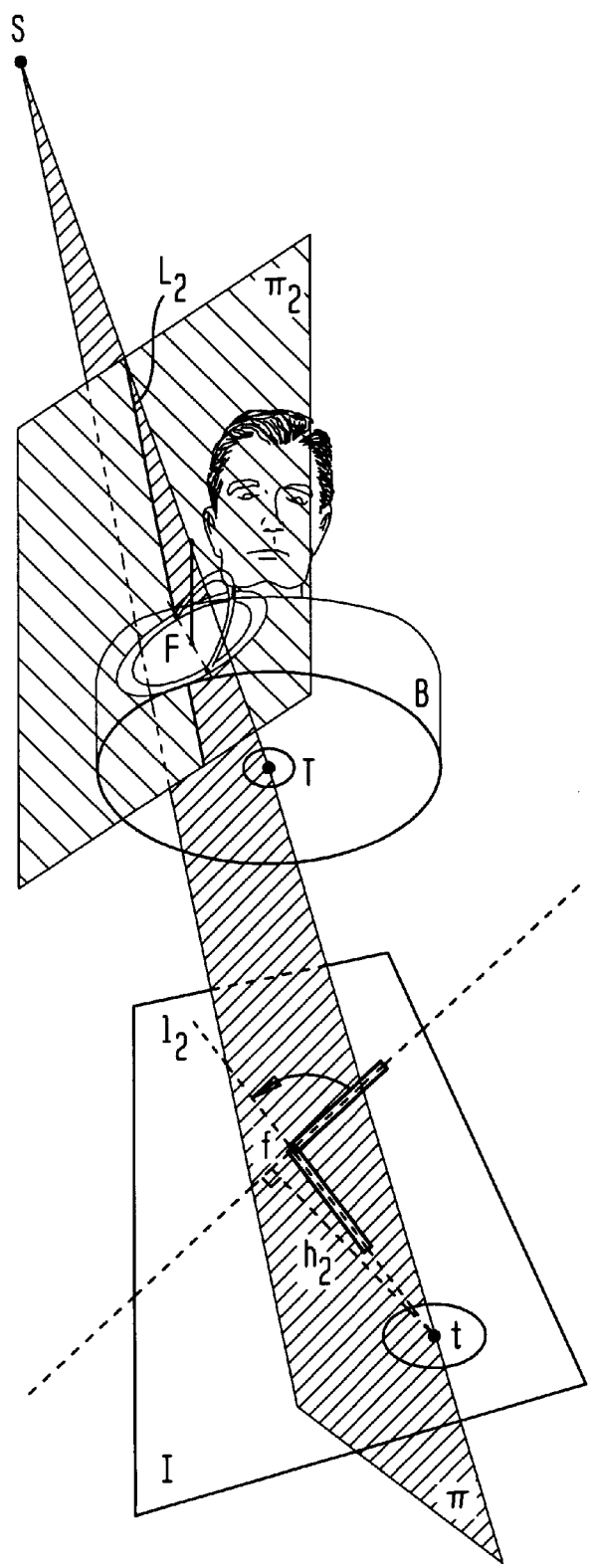
Figure 11:
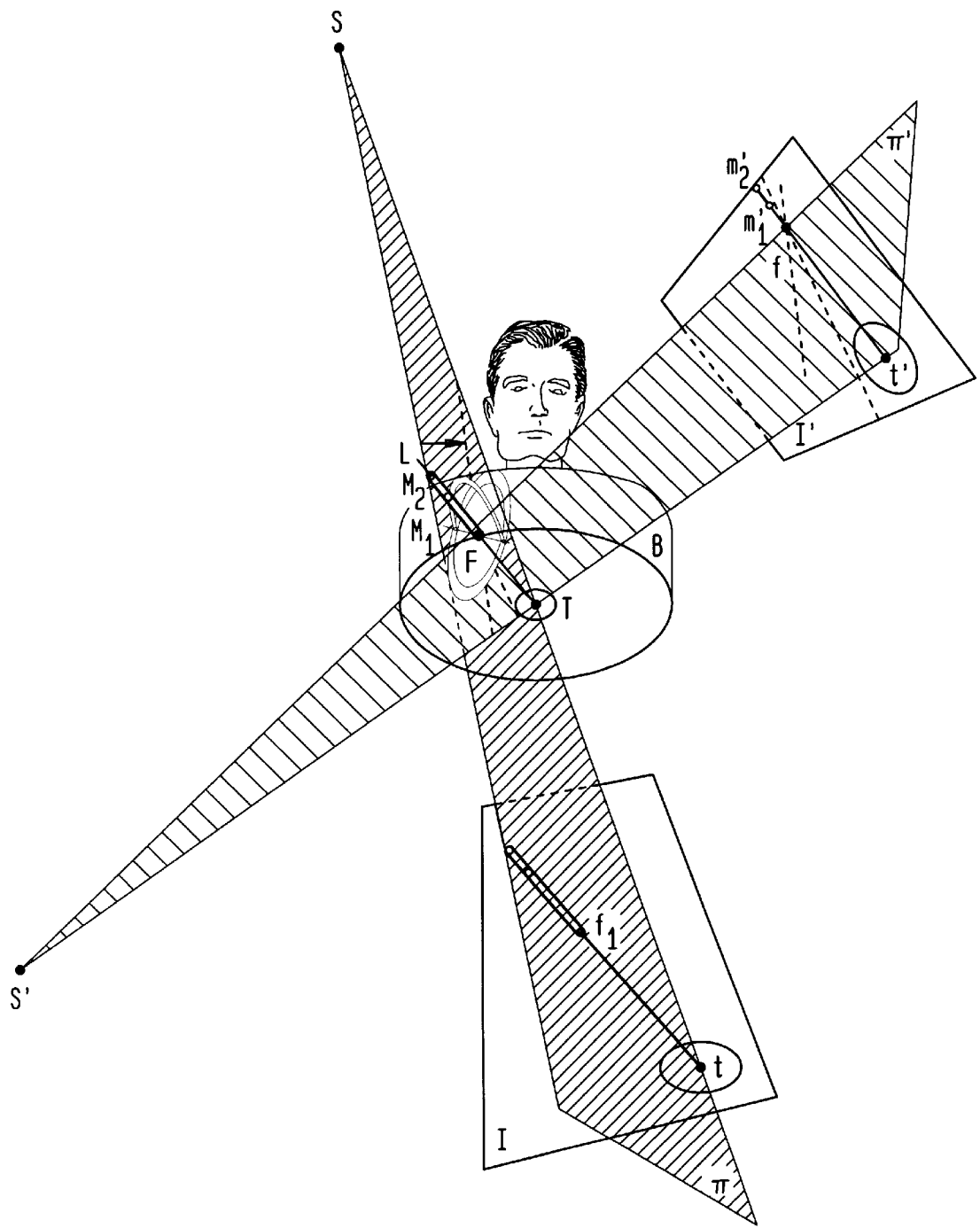
Figure 12:
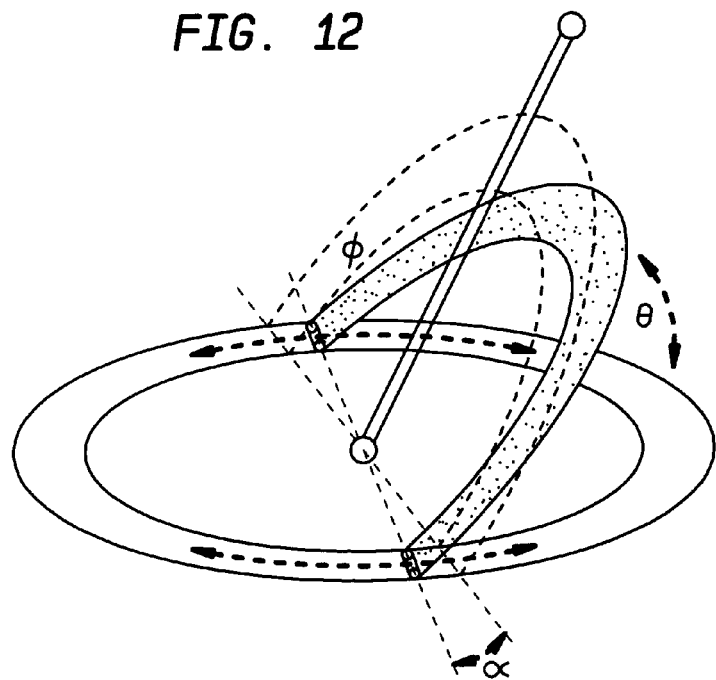
Figure 13:
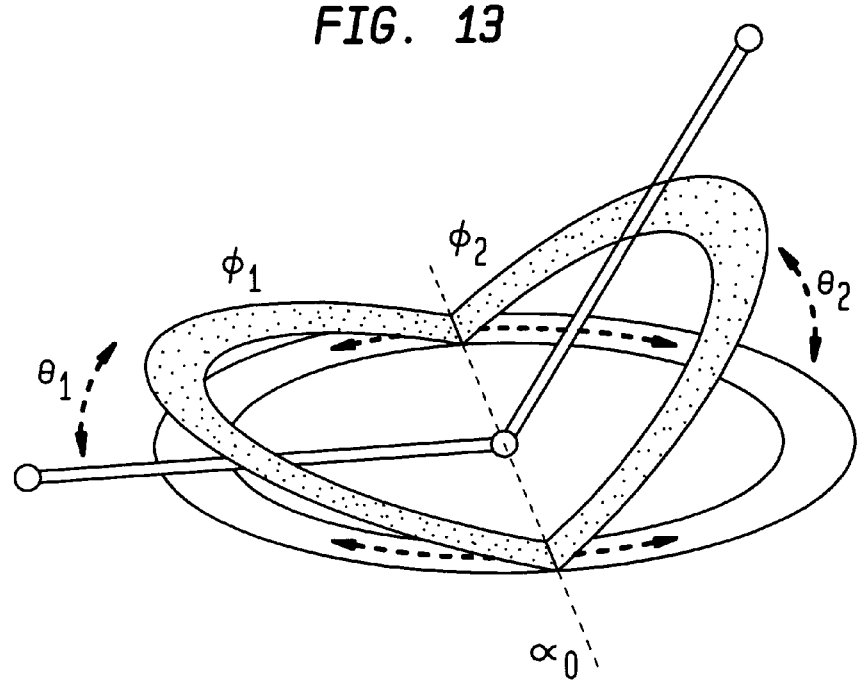
Figure 14:
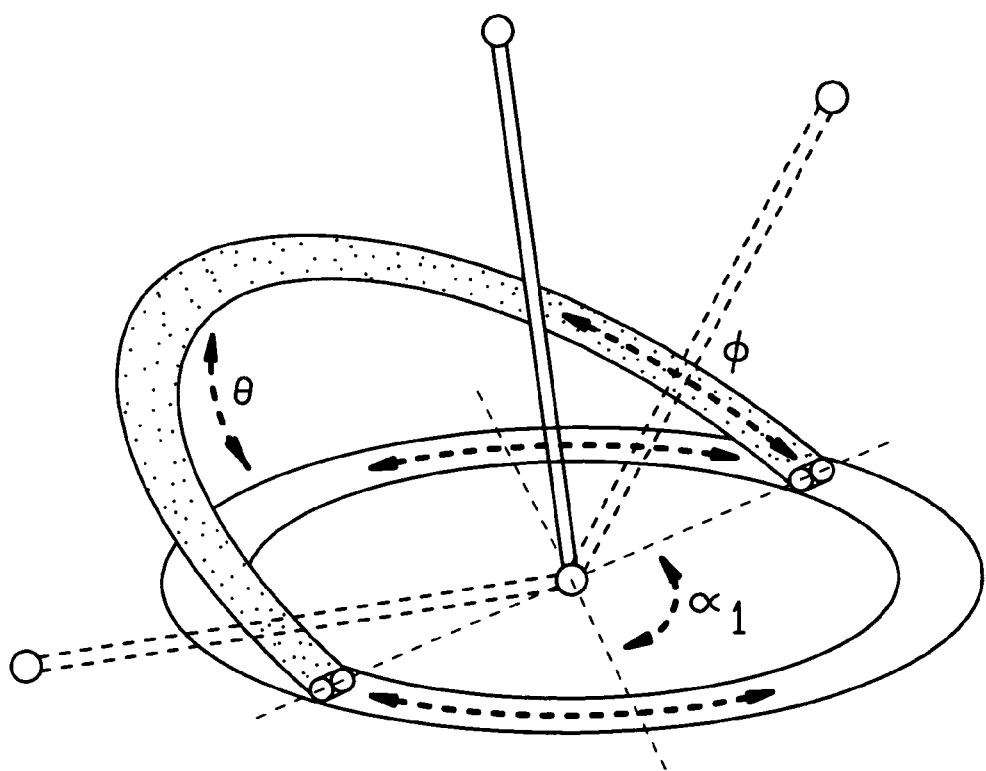
Figure 15:
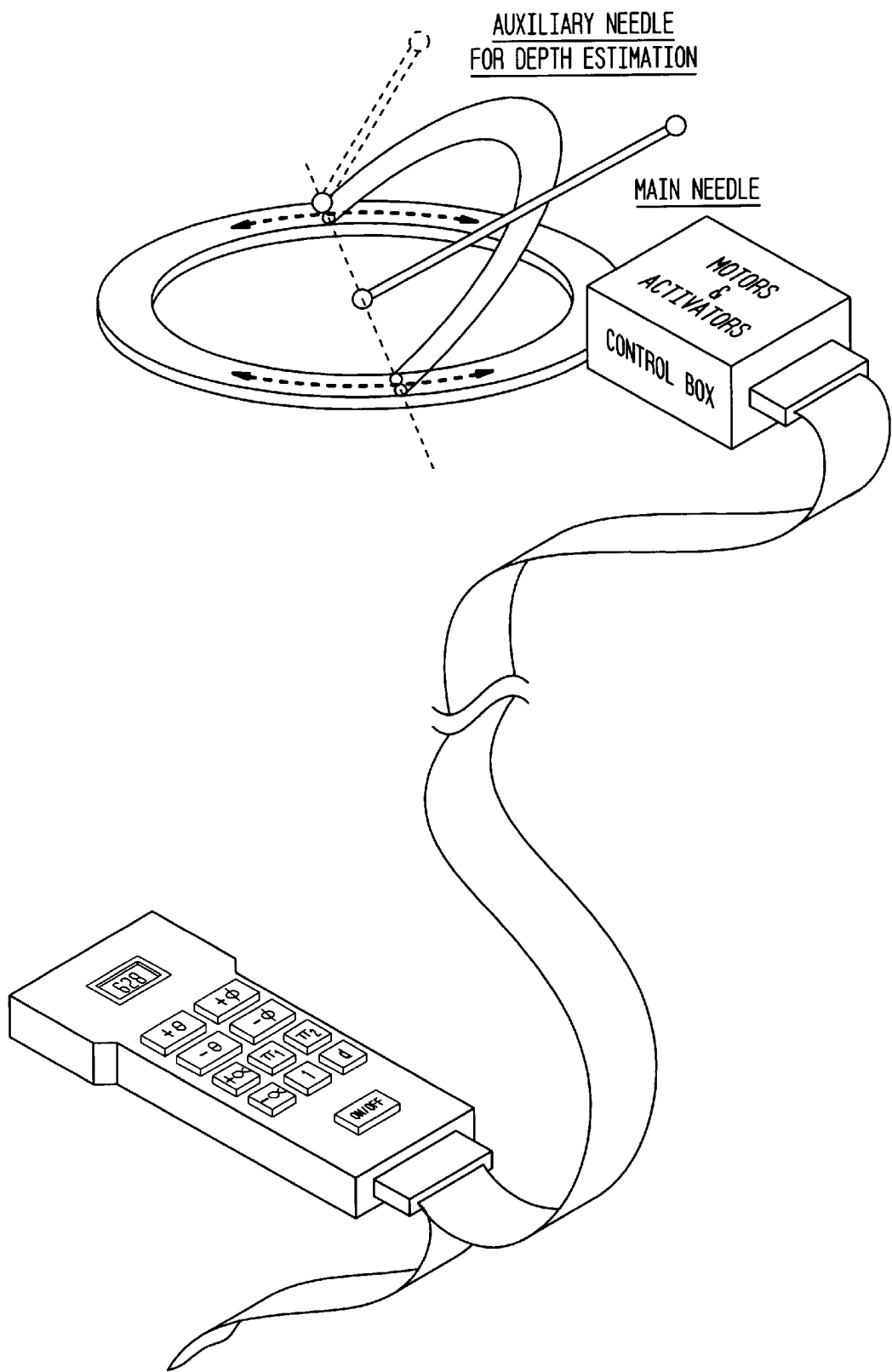
Figure 16:
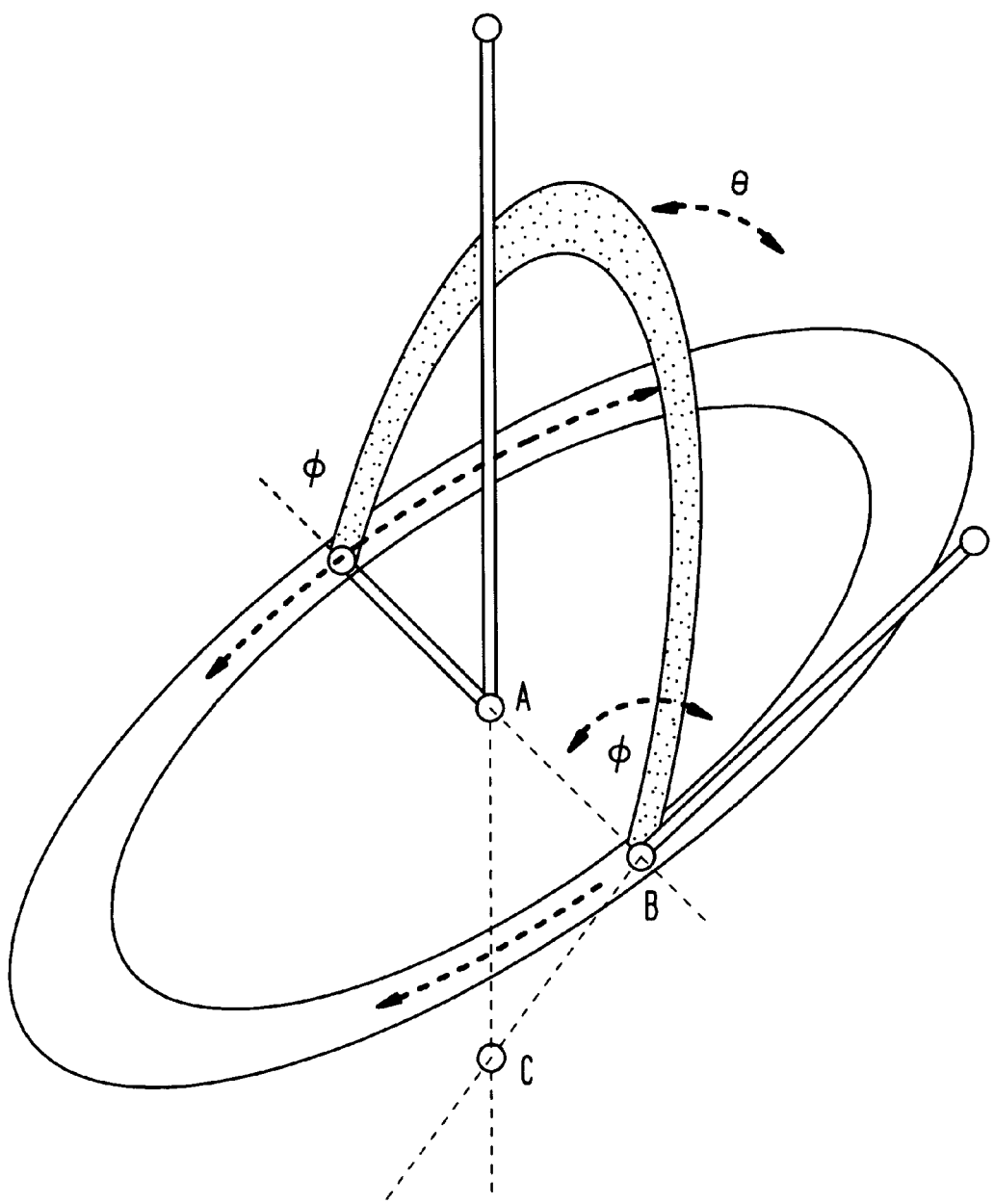
Figure 17:
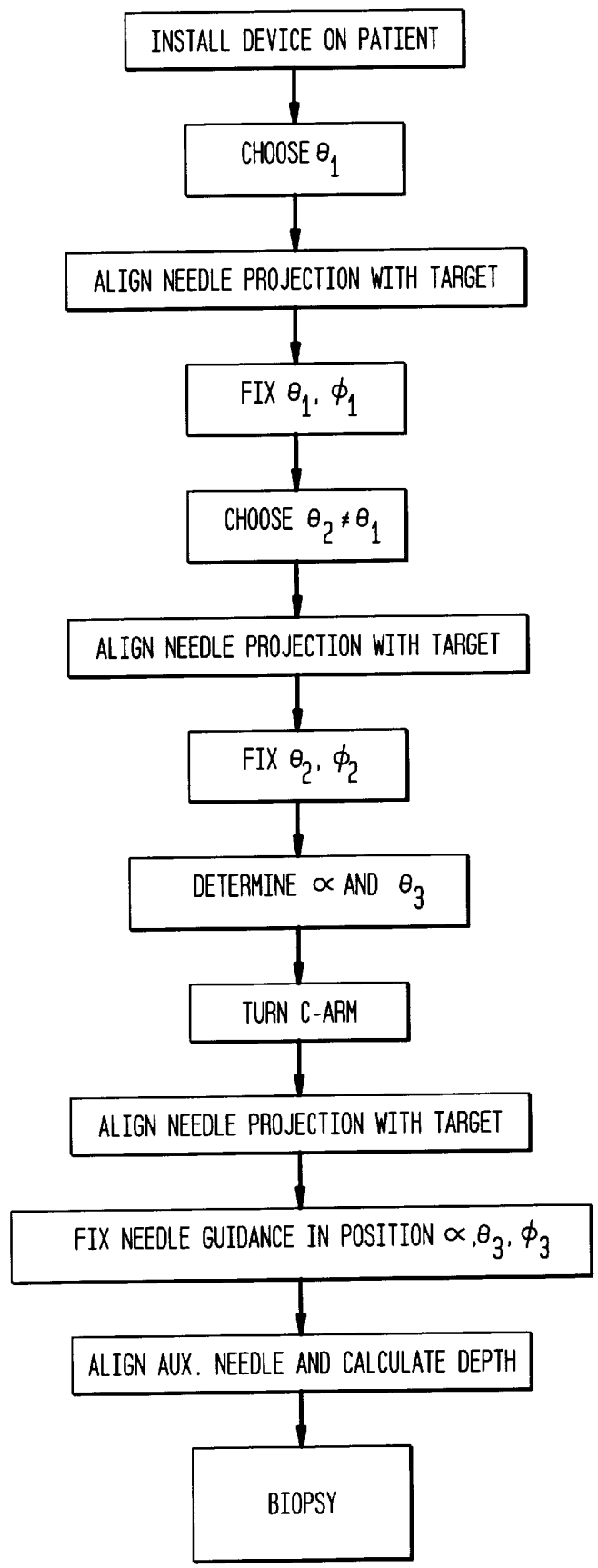
Figure 18:
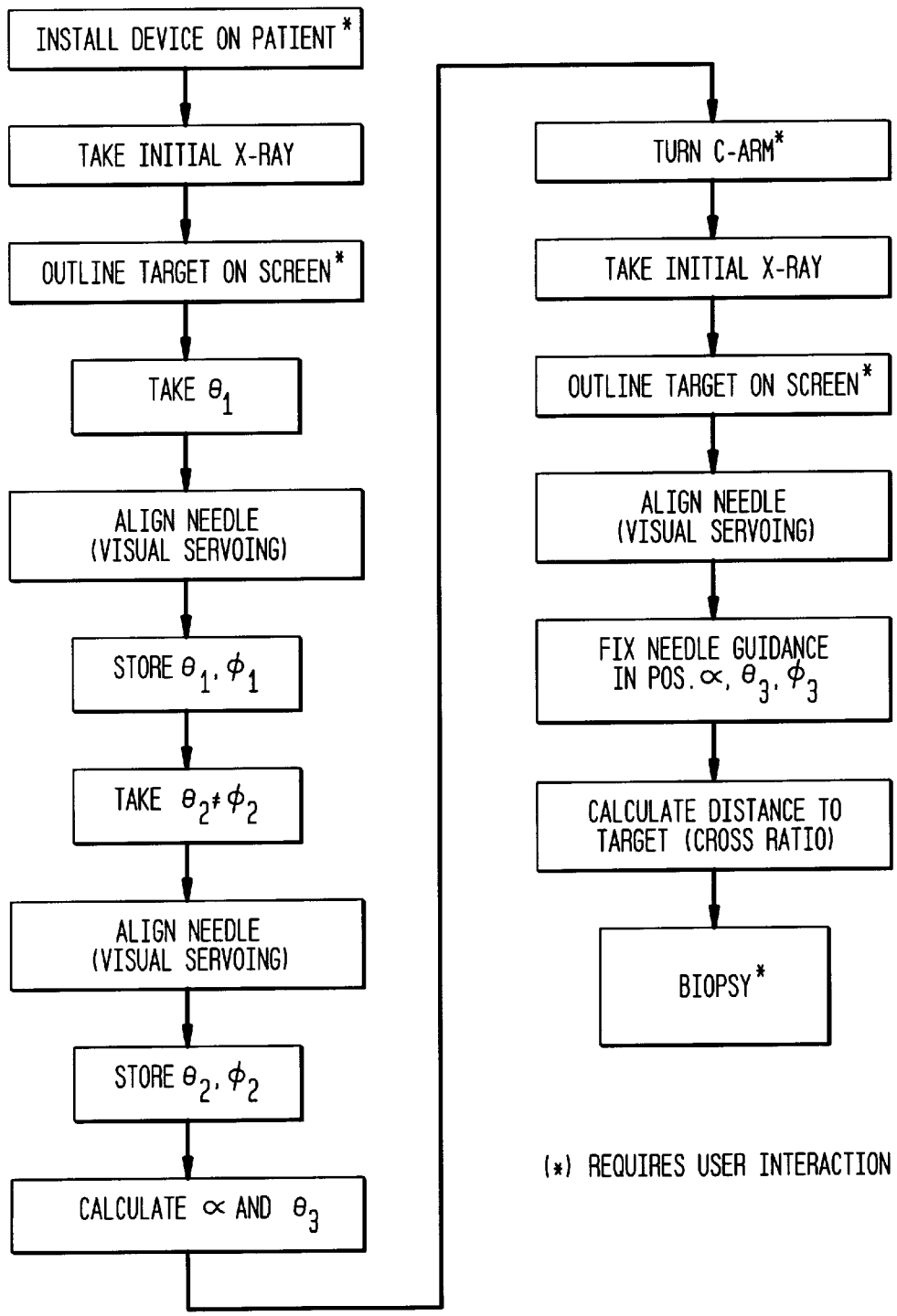
Figure 19:
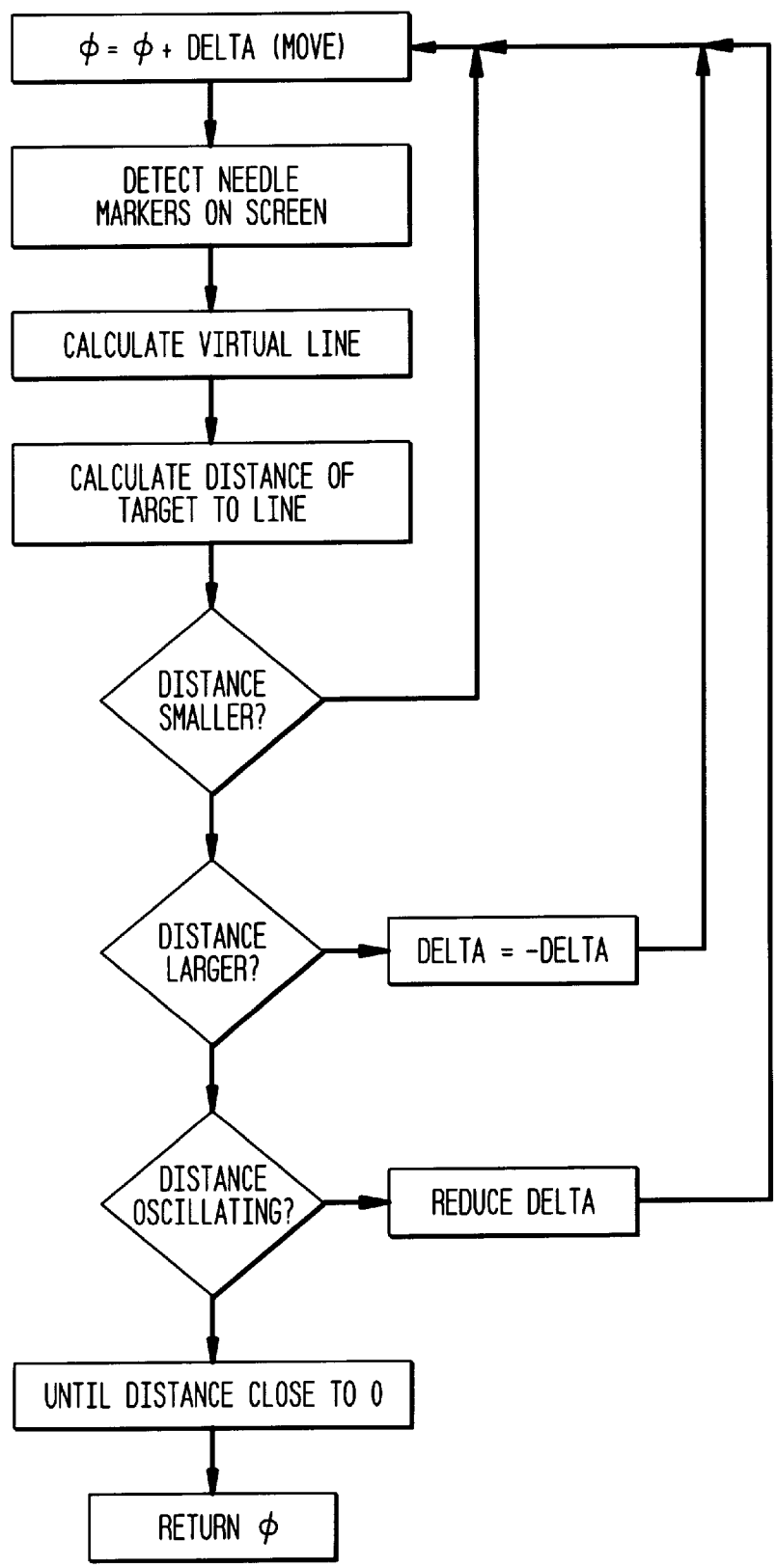
Figure 20:
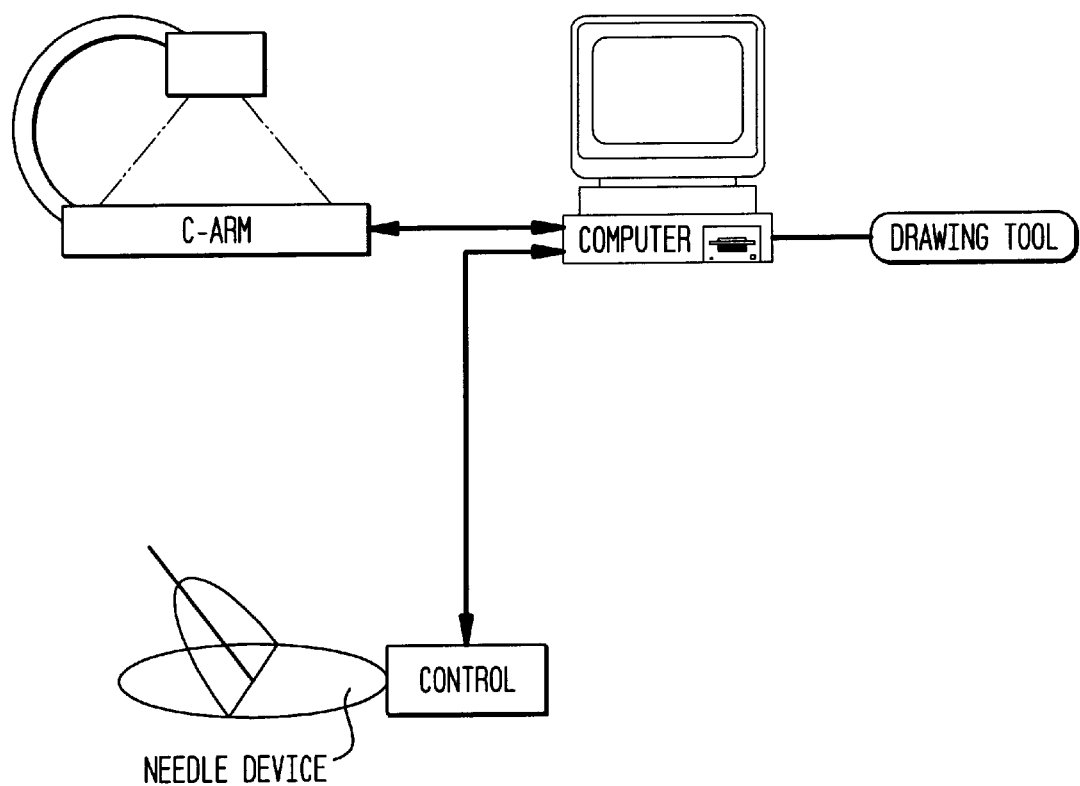
Figure 21:
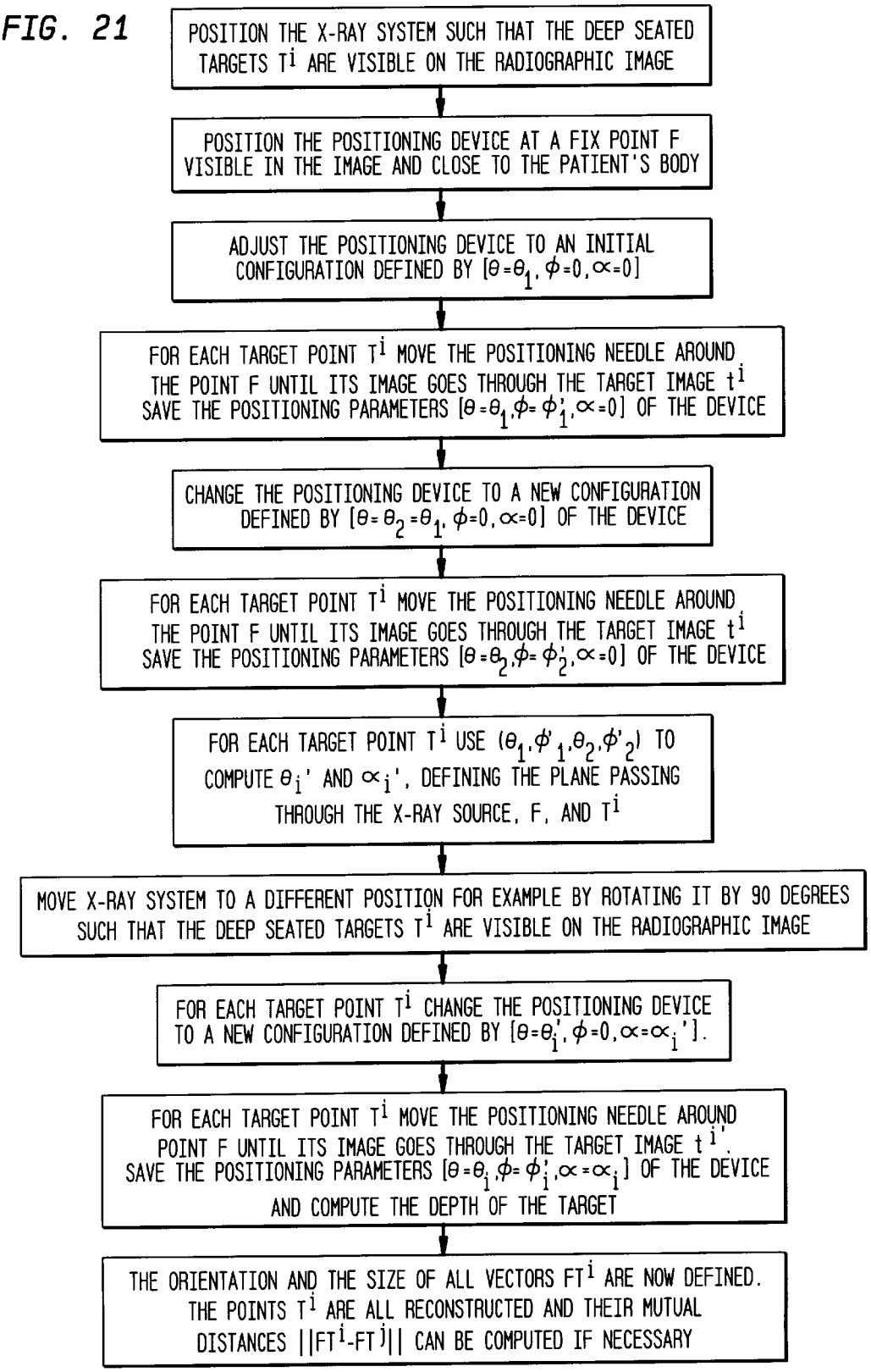
Figure 22:
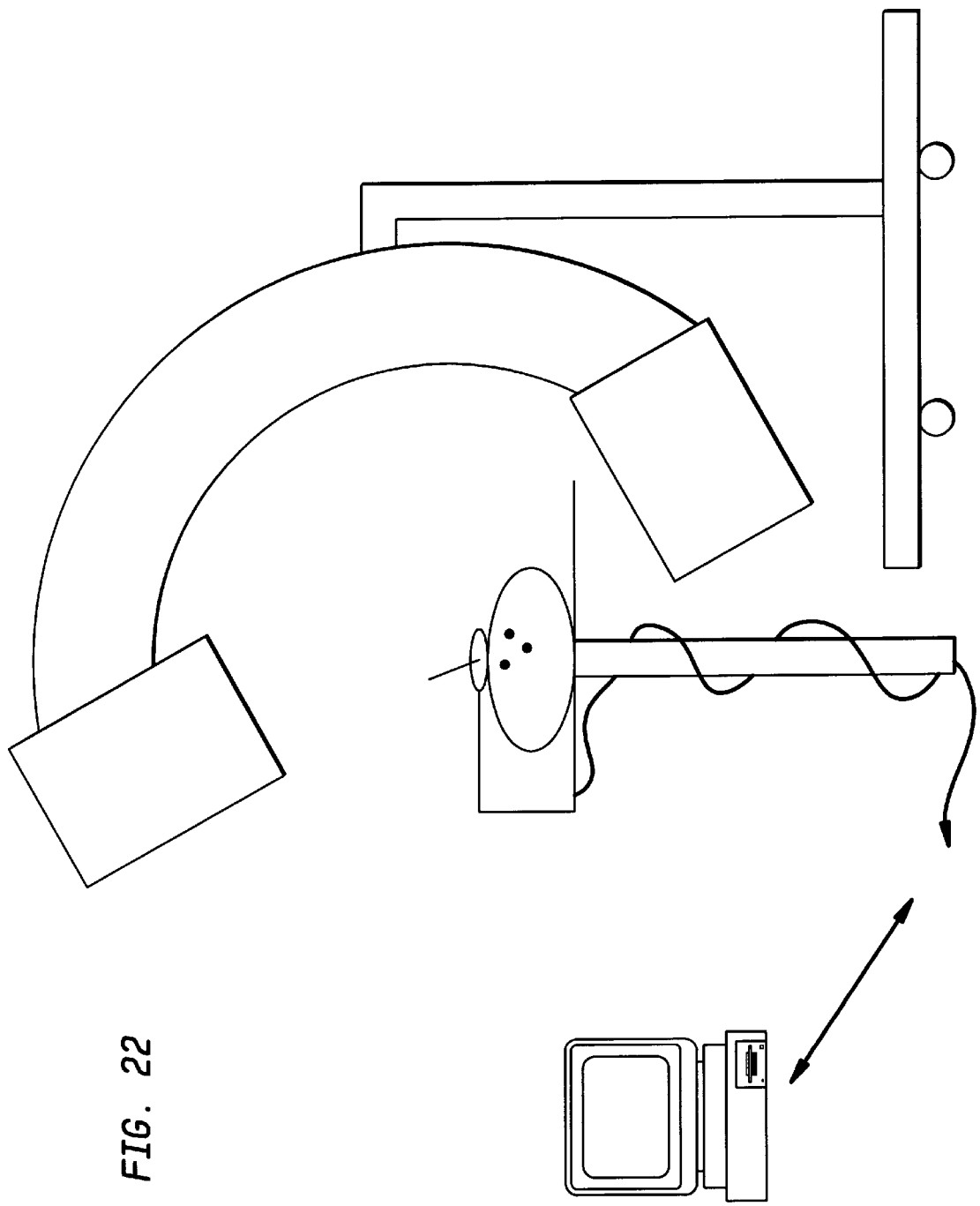
Figure 23:
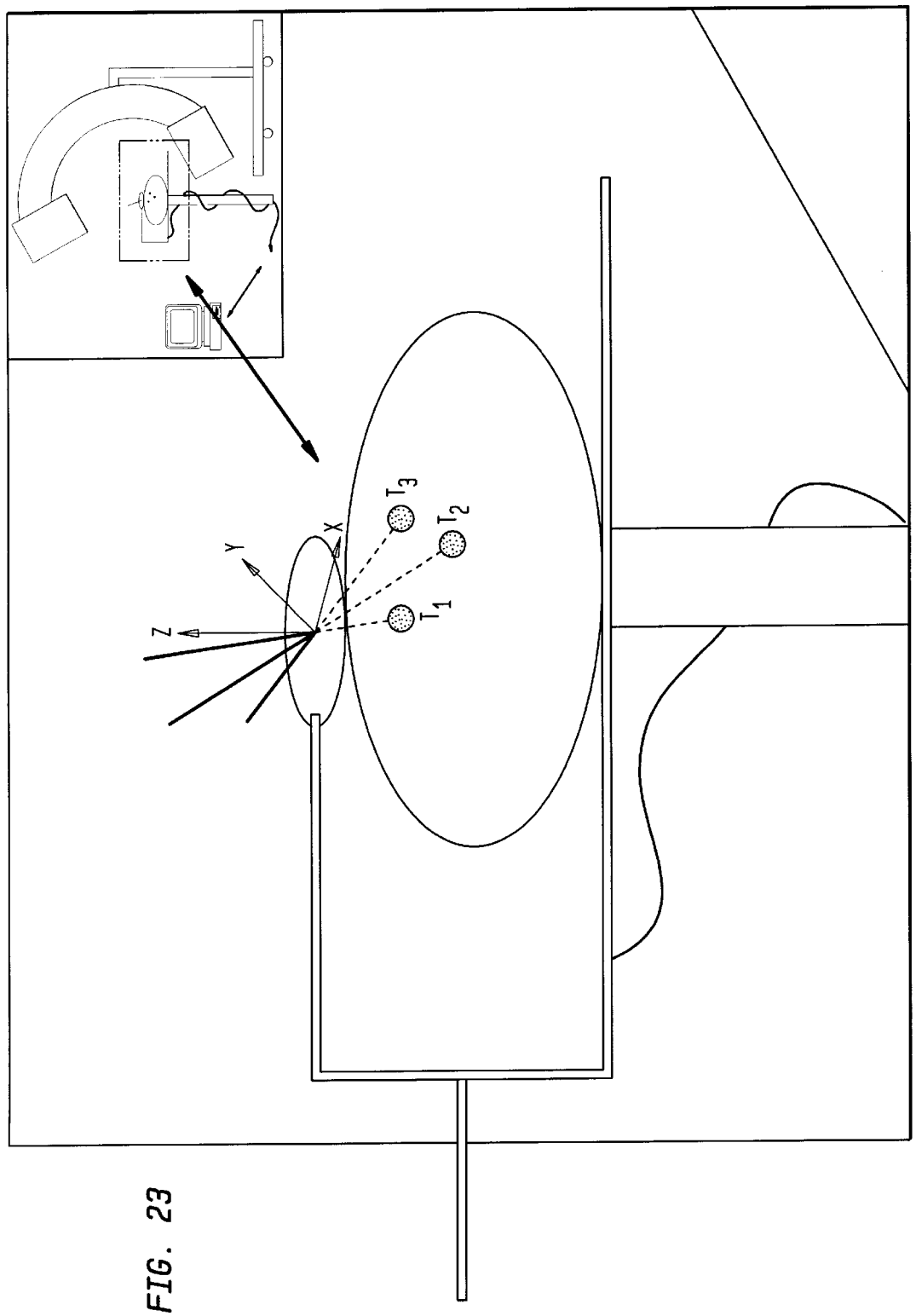
Figure 24:
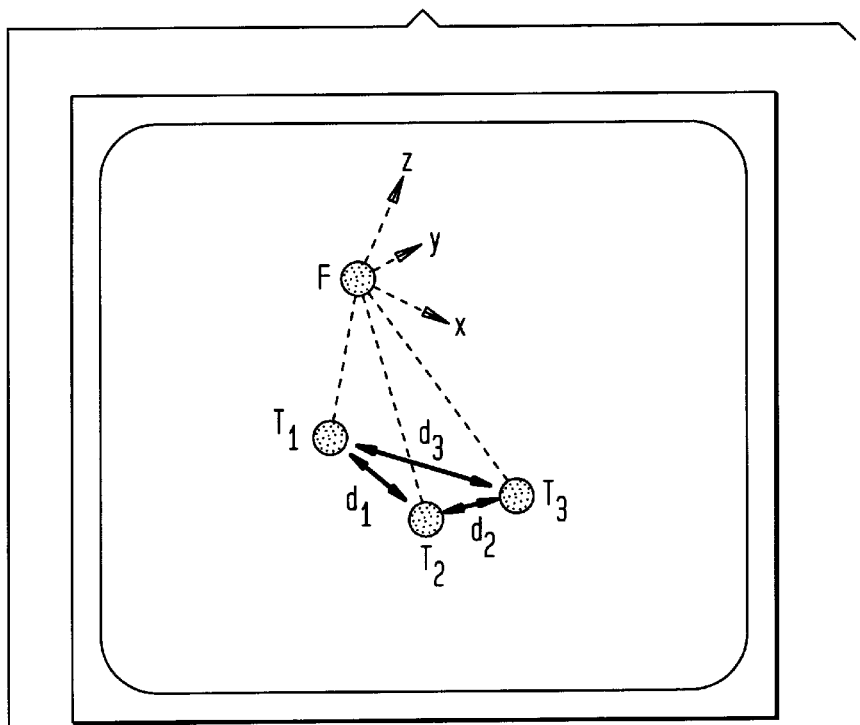
Figure 24:
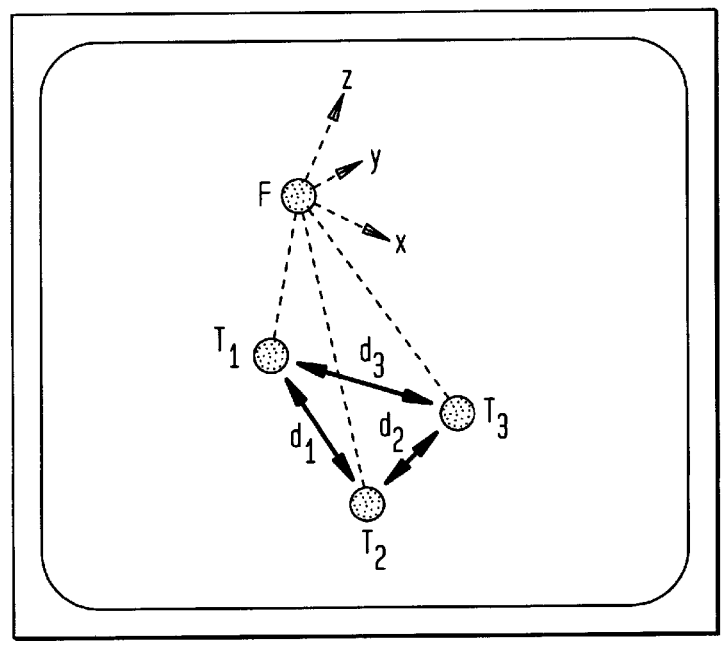

FIGS. 4, 5, and 6 show various steps of a method relating to the background and an example of a possible environment of the invention;

FIGS. 7 and 8 show diagrammatic representations of principles and apparatus relating to relating to the background and an example of a possible environment of the invention;

FIGS. 9, 10, and 11 show various steps of a method utilizable in conjunction with the invention;

FIGS. 12, 13, and 14 show diagramatically apparatus and principles relating to the background and an example of a possible environment of the invention;

FIG. 15 shows a system diagram relating to the background and an example of a possible environment of the invention;

FIG. 16 a diagrammatic representation of apparatus helpful to an understanding of the background and providing an example of a possible environment of the invention;

FIGS. 17, 18, and 19 show flow charts helpful to gaining an understanding of the background and an example of a possible environment of the invention;

FIG. 20 shows components of an automatic system and their interrelationship of a method utilizable in conjunction with the invention;

FIG. 21 shows a flow chart helpful to an understanding of the invention;

FIG. 22 shows in diagrammatic representation and not necessarily to scale an example of 3 targets inside a body to be reconstructed in accordance with the present invention; and FIGS. 23 and 24 show in diagrammatic representation and not necessarily to scale arrangements of an embodiment of the invention.

For a full and clear understanding of the present invention and the nature of the problem to which it is addressed, it is desirable to have a clear knowledge of the apparatus and method to which the invention preferably applies. As stated above, this apparatus and method for determining the correct insertion depth for a biopsy needle are disclosed in the above patent applications.

Accordingly, it is appropriate to review in some detail the principles of construction and operation of the apparatus for determining the correct insertion depth for a biopsy needle as in the above patent application in the name of Navab et al.

Figure 1:
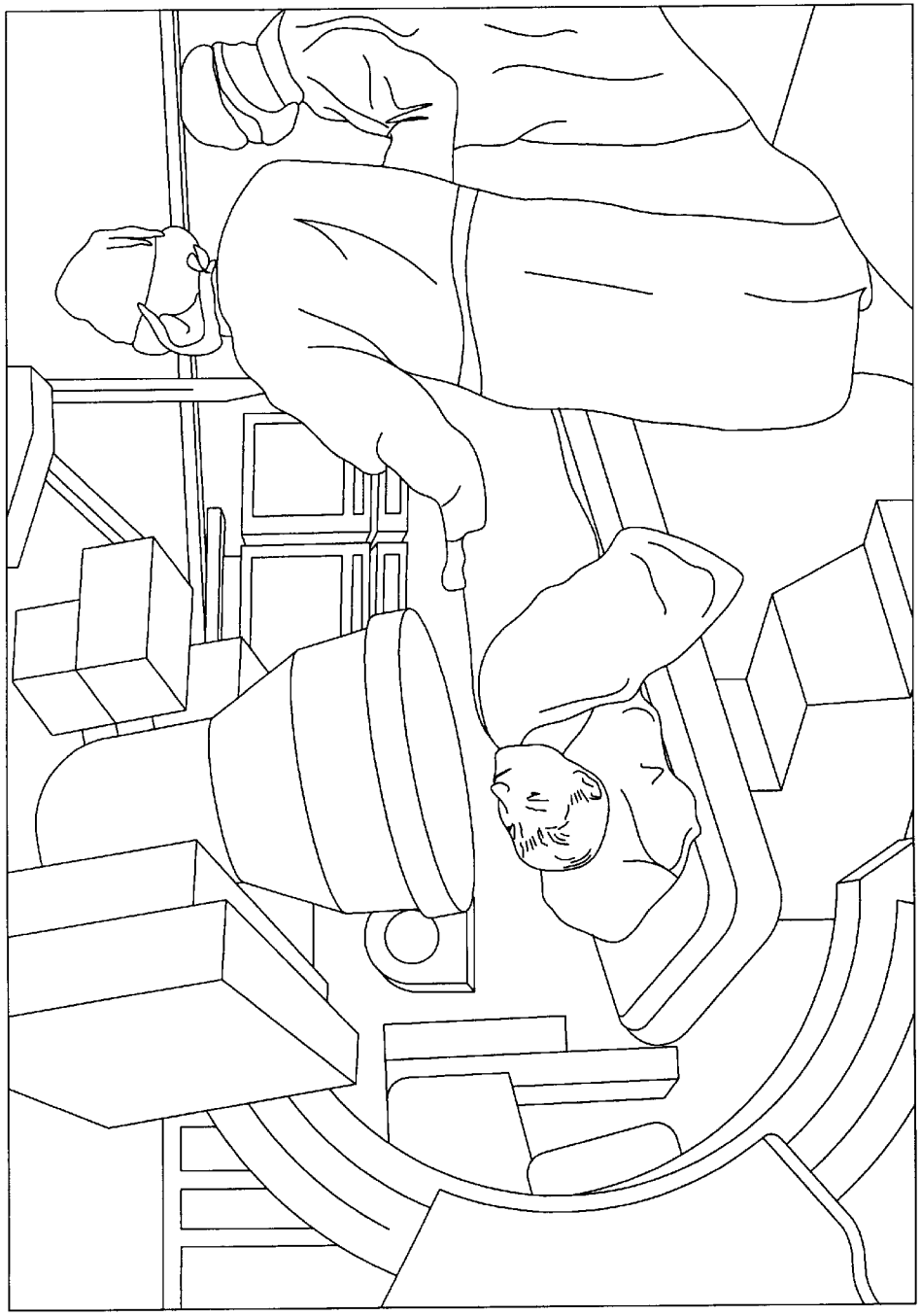
Figure 2:
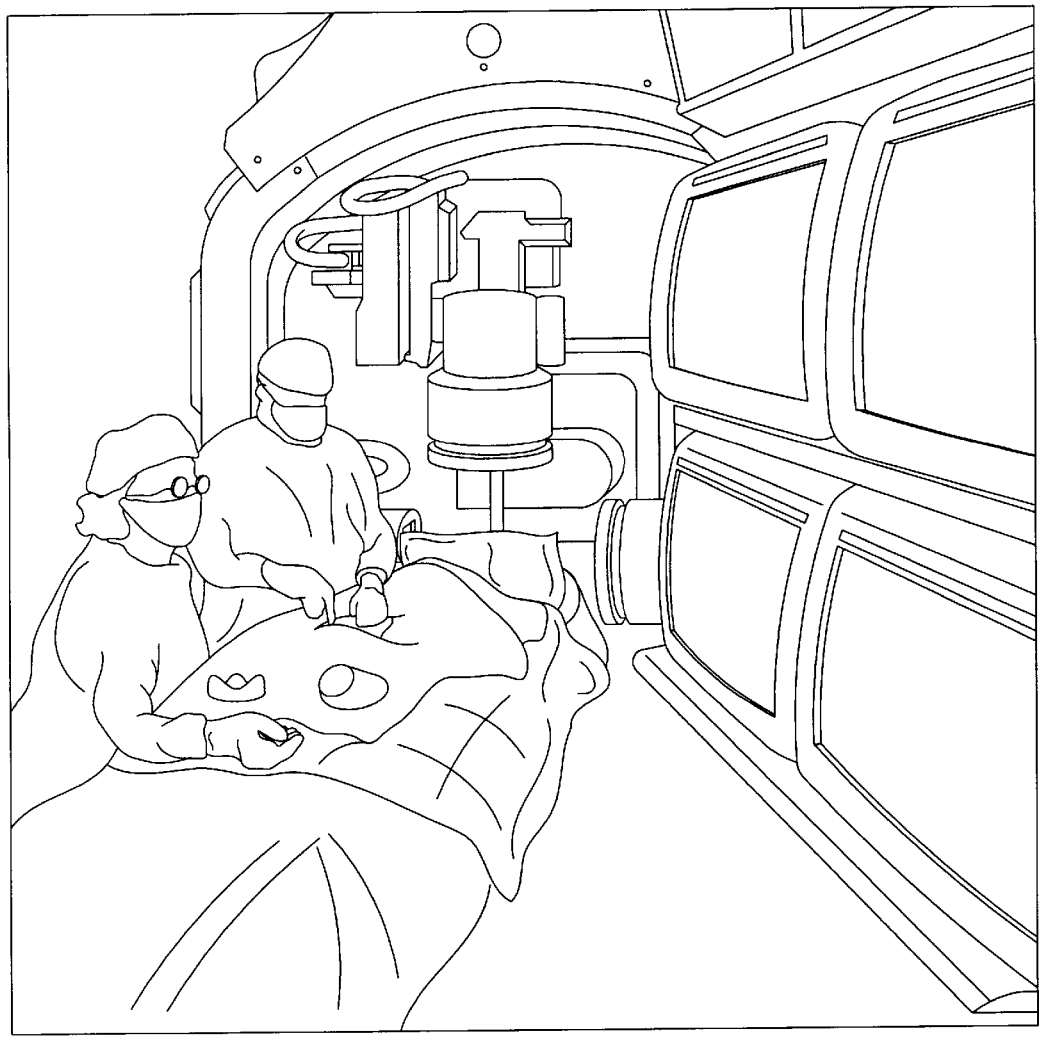
FIG. 2 shows a known type of fluoroscope with two simultaneous orthogonal views, such as may be utilized in conjunction with the present invention.
Figure 3:
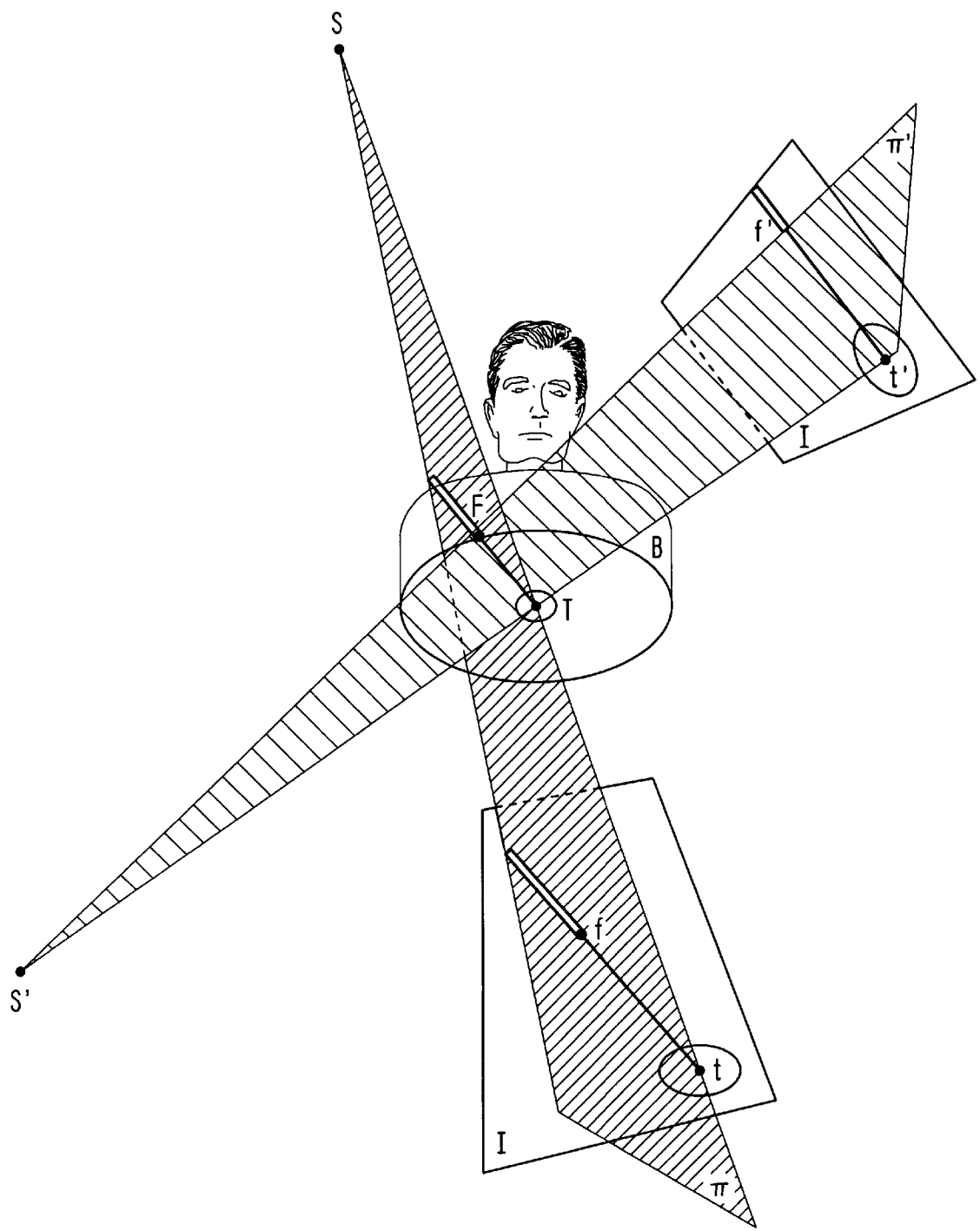
FIG. 3 shows a diagrammatic configuration of imaging radiation sources, image screens and a target area, relating to the background and an example of a possible environment of the invention.

FIG. 3 shows the geometry desirable for the surgeon. Preferably, the biopsy needle should be positioned such that its straight line continuation, or virtual extension, passes through a deep-seated target T inside the patient. During the manual procedure, the surgeon keeps the bottom end F of the needle on or near the patient's body and changes its direction until the virtual extension of the needle passes through the radiographic image t of the target T. The correct needle direction has to be verified on two radiographs that are taken from different angles.

As explained in the above-referenced patent application in the name of Navab et al., the apparatus has a geometrical configuration embodying a reasoned interpretation of what the surgeon seeks to do intuitively during a manual adjustment procedure. Clearly, the surgeon does not compute the exact or relative position and orientation of the C-arm and the image plane during a more or less refined "hit or miss" procedure. Rather, the surgeon proceeds by simple reasoning directly from radiographic images to the moving needle.

Referring again to FIG. 3, the imaging system, in accordance with the above-referenced patent application in the name of Navab et al. the apparatus for determining the correct insertion depth for a biopsy needle is modelled approximately as a "pinhole camera" model. The optical center, S, represents the location of the X-ray source and the position and orientation of an image intensifier defines the image plane, I. The deep-seated target inside patient's body is indicated by T, with t being its radiographic image.

F is a fixed point from where the surgeon wishes to insert the biopsy needle. f is its radiographic image. The viewing plane π is defined by the optical center, S, the target on the image, t, and the fixed point, F, and its radiographic image, f.

All the entities and reference letters relating to a second position of the X-ray and therefore to a second radiographic image are noted by prime, such as S', π', and so on.

Generally, images of all lines lying on the plane π which do not pass through the optical center S, are collinear to the line ft on the radiographic image I. Since the depth of the target T, or $\|FT\|$, is unknown, the maximum information that can be obtained on the position and orientation of the biopsy needle from a sequence of images taken from a single viewpoint is the three dimensional position of the plane π. Accordingly, a first part of the algorithm in accordance with the above-referenced patent application in the name of Navab et al. can be established, in accordance with the invention in Step I, as follows.

Any plane $\pi_1$ passing through the fixed point F, other than the plane $\pi$ itself, intersects the plane $\pi$ in one line. This line clearly contains the point F and therefore its image must pass through the image f of the fixed point F on the image on image plane I. The first two steps of the algorithm can now be defined, resulting in a method of accurately obtaining the three dimensional coordinates of the viewing plane $\pi$. A metallic, or other radiation-opaque, bar is rotated around the fixed point F in an arbitrary plane $\pi_1$ passing through the fixed point F. See FIG. 4, which illustrates the step of finding a three-dimensional line lying on the viewing plane $\pi$. The shortest distance of the projection line of the three-dimensional line from the target t on the image is called $h_1$.

This $h_1$ distance decreases as the angle between them closes, and projection line approaches line $L_1$, representing the intersection of the planes $\pi$ and $\pi_1$, and vanishes at the intersection of these two planes. This provides a simple way to control the metallic bar under automatic images guidance and move it until it lies on the plane $\pi$.

In a further step, Step II, in accordance with the apparatus and method for determining the correct insertion depth for a biopsy needle, a metallic (X-ray opaque) bar is rotated around the fixed point F in a second plane $\pi_2$ passing through the fixed point F, and different from $\pi_1$ used in the Step I, see FIG. 5, which illustrates the procedure for finding a second three-dimensional line on the viewing plane $\pi$.

Preferably, the plane passing through F and orthogonal to $\pi_1$ is selected as $\pi_2$. The distance of its projection line from the target t on the image, is called $h_2$. This distance decreases as the projection line of $\pi_2$ approaches line $L_2$, representing the intersection of the planes $\pi$ and $\pi_2$ and this distance, $h_2$ vanishes at the intersection line of these two planes.

This provides a way to control a second metallic bar under automatic images guidance and move it until it also lies on the plane $\pi$. Now two distinct lines, $L_1$ and $L_2$, having a non-zero angle of intersection therebetween, are identified on the plane $\pi$. These lines uniquely define the plane $\pi$ in three dimensional space. This is the maximum information that can be had from a single viewpoint with no calibration data.

A next step in accordance with the apparatus and method for determining the correct insertion depth for a biopsy needle disclosed in the above patent application to Navab et al., Step III, is the use of a second viewpoint. The radiographic image from a second viewpoint can be obtain either by moving the C-arm of the machine arbitrarily; the larger is the angle of rotation the more accurate is the resulting position and orientation of the needle. The plane defined by the optical center, the X-ray source S' of the new configuration of the imaging system, the target T and the fixed point F is designated as $\pi'$, analogous to plane $\pi$ in the previous determination. See FIG. 6 which shows the procedure for finding the right orientation for the biopsy needle.

A metallic bar is rotated around the fixed point F in the plane $\pi$ obtained in step II. The distance of its projection line, l', from the target t' on the image taken from the new viewpoint, is called h'. This distance decreases as one gets closer to the line L', representing the intersection of the planes $\pi$ and $\pi'$ and this distance vanishes at the intersection of these two planes.

This provides a way to control the metallic bar manually or automatically using image guidance and move it until the line FT is found. FT is the line of intersection of the two flat planes $\pi$ and $\pi'$ and it therefore represents a vector direction in space passing through the proposed fixed insertion point F and, when produced, through the target T. Now, the surgeon can be guided to the correct positioning of the biopsy needle. The next step in accordance with the invention, Step IV, is to let the surgeon know how deep the target T is inside the patient.

The cross ratio is a fundamental invariant of perspective projection. See, for example, O. D. Faugeras, Three-Dimensional Computer Vision: A Geometric Viewpoint; MIT Press, Cambridge, Mass.; 1993. This invariant can be used here to accurately compute FT, the depth of the target inside patient's body.

Referring to FIG. 7, consider the four points A, B, C, and D, on a line in space. The cross ratio of these four points can be defined as $$\frac{AB \times CD}{AC \times BD}.$$

The perspective projection of these four points on any plane and with respect to any projection center, for example {a,b,c,d} and {e,f,g,h} in FIG. 7 results in the same cross ratio between the projected points:

$$\frac{AB \times CD}{AC \times BD} = \frac{ab \times cd}{ac \times bd} = \frac{ef \times gh}{eg \times fh}$$

For the case of two markers, $M_1$ and $M_2$, on the metallic bar used in step III, such that $\|M_1F\|$ and $\|M_2F\|$ are accurately known, and $m_1'$ and $m_2'$, their radiographic images, are easily and accurately detectable, see FIG. 8. The assumptions made are reasonable and readily realized in practice. The cross ratio computed for the image points [m'1, m'2, f', t'] is the same as the cross ratio of the four points [$M_1$, $M_2$, F, T] in the three dimensional space. The positions of all these points other than T are known. FT is then computed from the following equation:

$$\|FT\| = \frac{\lambda \times \|M_1F\| \times \|M_2F\|}{\|M_1M_2\| - \lambda \times \|M_1F\|}$$

$$\text{where } \frac{\left\|\frac{\|f't'\|}{m_{2'}t'}\right\|}{\frac{\|m_{1'}f'\|}{\|m_{1'}m_{2'}\|}}$$

The positioning in accordance with the apparatus and method for determining the correct insertion depth for a biopsy needle disclosed in the above patent application to Navab et al. is designed based on the algorithm disclosed above. FIGS. 12, 13, 14, and 16 show a design configuration. A part of the apparatus is a semi-circle that can rotate at least from 0 to 180 degrees around the center of a circular base. This rotation angle is designated by $\alpha$ in FIG. 12. This semi-circle has a second degree of freedom: it can also turn around its own baseline from 0 to 180 degrees. This rotation angle is designated by $\Theta$ in FIG. 12. A metallic bar can rotate on the plane defined by this semi-circle from 0 to 180 degrees. This rotation angle is noted by $\phi$ in FIG. 12. In accordance with the invention, this provides all that is required. All rotations can be done either by hand, by command, or automatically. The parallel or serial connection between a computer, such as a personal computer (PC), and a positioning device can guide the system based on the minimization of $h_1$, $h_2$ and h' on the radiographic images. Further details about the interactive and automatic process are provided in appendix-A and appendix-B.

FIGS. 9, 10, and 11 provide bridging information to facilitate an understanding of the relationship between the foregoing algorithm and the design herein described. These figures include some of the constructions shown in previous figures and are helpful to bridging the steps between the geometric principles forming a basis for the present invention and the practical apparatus and method herein disclosed.

FIG. 9 shows the procedure utilized in finding one three dimensional line lying on the viewing plane π. This comprises positioning the semi-circle at an arbitrary position to define a plane $\pi_1$ and then moving the metallic bar mounted on the semi-circle to a position where its image passes through f and t on the image. This process can be done automatically. The metallic bar is moved to minimize the distance $h_1$ on the image. This process is not time-consuming and is readily carried out in real time.

FIG. 10 shows Step II, the process of finding a second three dimensional line lying on the viewing plane π. This is similar to the previous step, but the semi circle has turned by an angle in the order 90 degrees around its based line defining a new plane $\pi_2$.

FIG. 11 shows Steps III \& IV: Finding the right orientation of the biopsy needle and the depth of the target T inside the patient's body. This comprises positioning the semi-circle in the plane, π' defined by the metallic bar in steps I and II, and then rotating the metallic bar until its radiographic view from the new viewpoint passes through f' and t'. The center of the circular base, F, and the target inside patient's body, T, lie on the both planes π and π'. Their intersection is therefore FT the correct direction of the biopsy needle. The depth of the target, |FT|, can then be computed using the invariance of cross ratios by perspective projection; see the previous section on the geometrical description. The whole process, steps I through IV, can be done in real time and the surgeon can easily move the device and find the new orientation of the biopsy needle and depth of the target at any other contact point on the patient's body. This design lends itself readily to economical implementation.

The interactive system in accordance with the present invention has the advantage of being an independent unit which can be used together with any kind of X-ray fluoroscopes or C-arm imaging system and it needs no physical connections with the imaging system. The unit is entirely and readily portable. Furthermore, the operating surgeon has no radiation exposure at all during the search for the correct position.

FIG. 15 shows a protocol for the interactive system as herein described. In this case the apparatus is fixed on the patient on top of the desired entry point defined by the surgeon. The surgeon works with the control device while looking at the radiographs and can be in the same room or in another room where the radiographic images can be observed without the surgeon's being exposed to the radiation.

These are the consecutive steps of the process in accordance with the apparatus and method for determining the correct insertion depth for a biopsy needle disclosed in the above patent application to Navab et al.:

A first plane is taken by fixing α=0 and $\Theta = \Theta_1$. See FIG. 13. Note that $\Theta_1$ is quite arbitrary. A user can choose this plane so as to maintain a clear view of the metallic bar. This can be done using the control buttons, $\pi_1$, +α, −α, +Θ and −Θ, as shown in FIG. 15.

The user then selects the proper angle φ by moving the metallic bar until its radiographic image passes through the target point. This can be done by using buttons +φ and −φ as in FIG. 15. The orientation of the metallic bar is then defined as:

$$L_1 = [\sin(\phi_1)\sin(\phi_1), \sin(\phi_1)\cos(\theta_1), \cos(\phi_1)]]$$

See FIG. 13. Note that $\Theta_2$ is also arbitrary. A user can choose this plane in order to have a clear view of the metallic bar. This can be done using the control buttons, $\pi_2$, +Θ, and −Θ, as in FIG. 15.

A user finds the right angle φ by moving the metallic bar until its radiographic image passes through the target point. This can be done by using buttons +φ and −φ, as in FIG. 15. The orientation of the metallic bar is then defined as:

$$L_2 = [\sin(\phi_2)\sin(\theta_2), \sin(\phi_2)\cos(\theta_2), \cos(\phi_2)]$$

where
n=L∧L'

The final viewing plane (see FIG. 14) is then defined by $$\alpha = \arccos\left(\frac{n_y}{c}\sin(n_z)\right) \text{ and}$$

$$\theta = -\arccos\left(\frac{c}{\|n\|}\right)\sin(n_x(\sin(\alpha)n_z + \cos(\alpha)n_y)) \text{ where}$$

$$n = L \wedge L' \text{ and}$$

$$c = \sqrt{(L_x L'_z - L_z L'_x)^2 + (L_y L'_x - L_x L'_y)^2}$$

and ∧ is the vector product defined in $R^3$.

The system will automatically move to the right position and the user has no need to adjust Θ and α in this case.

The user then uses the image on the second image intensifier or moves the C-arm to a new position.

The user finds the proper angle φ by moving the metallic bar until its radiographic images passes through the target point. This can be done by using buttons +φ and −φ as shown in FIG. 15. This is the correct orientation of the needle to be used for the biopsy.

In order to compute the depth of the target in this case, two other auxiliary needles are placed on the base line of the semi-circle; see FIG. 16. In order not to disturb the image of the main needle, these needles can be made in acrylic (transparent to X-ray) with only a few metallic markers to be aligned with the deep seated target. The determination of depth is arrived at by a process of triangulation in which a base-line forms the base of a triangle with the directions of the other two sides of the triangle being determined by respective angles subtended by the base and the respective side. Accordingly, the accuracy is greater where the angle between a needle and the metallic bar is greater. Hence, two alternative needles are provided so that needle is utilized which is on the side of the obtuse angle made by the metallic bar with the plane of the diameter of the semicircle.

Each of these needles can rotate in the plane defined by this semi-circle around a fixed point other than the entry point. In accordance with the present embodiment, the two end points of the base line are used as the two centers of rotation. In the final position, the plane defined by the semi-circle also includes the deep seated target.

Once the correct orientation of the needle is found, the system activates that one of the auxiliary needles which has the greater angle with the main needle. The user moves this needle to align it with the target on the image. The system computes the depth of the target by computing the distance between the entry point and the intersection of the main needle and the active auxiliary needle. FIG. 16 shows this construction in detail.

The depth to the target, AC, is given by the trigonometric formula $$AC = \sin(\phi_1) \times \frac{AB}{\sin(\phi_1 - \phi)}$$

FIG. 17 shows a flowchart of the interactive process in accordance with the principles of the apparatus and method for determining the correct insertion depth for a biopsy needle disclosed in the above patent application in the name of Navab et al.

A semi-automatic system reduces the human interaction to the initial fixation of the unit on the patient, a definition, such as a manual definition, of the tumor on a computer display, and the final insertion of the needle, that will remain fully under the control of the surgeon.

The search for the optimal needle position and the calculation of the target depth is done automatically. The benefits of such a system are substantially increased speed of operation and thus less patient discomfort, reduced risk of patient motion, reduced radiation for the patient, and complete elimination of radiation for the surgeon during the search for the position.

The automatic system utilizes as a starting point the same basic arrangement as the manual version with additional features. Three effectors are included, such as drive motors, to change the needle position. One each is utilized for $\Theta$, one for $\phi$, and one for the rotation $\alpha$, respectively. X-ray opaque markers are provided on the biopsy needle guidance so as to be visible on the fluoroscopic images and to be readily detectable by an image processing unit.

A computer is linked to the fluoroscope so as to be able to capture and store the X-ray images and to perform the necessary image processing to detect the needle markers. A computer stores and calculates needle positions and commands the effectors so as to move the needle position. Furthermore, a user interface to the computer allows the surgeon to draw the outline of the target on the fluoroscopy image with a computer "mouse" coordinate translator or by using a graphics tablet.

Essentially, the procedure is as follows for the apparatus and method for determining the correct insertion depth for a biopsy needle disclosed in the above patent application in the name of Navab et al. The unit is installed on the patient. One single image from the fluoroscope is stored and displayed on the computer screen. The surgeon outlines manually the tumor on this image using the mouse. During this stage of the interaction, the fluoroscope is turn off, thereby reducing radiation exposure. The computer selects a first plane $\Theta$ and performs a task that is known as visual servoing. See FIG. 18. It changes the needle position, thereby varying $\phi$ and detects the needle markers on the fluoroscopic image. From the markers, it can determine the projection of the needle, that is the axial center-line of the needle produced or continued beyond the needle.

The closest distance of this "virtual needle" to the target in the image can be calculated. The position of the needle is changed until this distance is reduced to a minimal amount and the projection of the needle passes through the target. The parameters $\Theta$ and $\phi$ of the needle position are stored. This step is repeated for a different choice of $\Theta$ in order to find a second needle position. Then the C-arm position has to be changed, and the target must be outlined once again on a first image. From the two previous needle positions, the computer calculates the necessary rotations $\alpha$ and $\Theta$ to bring the needle in the final plane.

Then the visual servoing step is repeated. The final position $\phi$ is the one that passes through the target. The needle guidance system has to be blocked in that position, either using the effectors or by actuating an additional blocking or position locking device. The fluoroscopy unit is switched on for two initial images that are used for outlining the target, and during the visual servoing steps. This procedure is usually very brief. The system then uses the needle markers in order to automatically compute the depth of the target from the entry point. Depending on the speed of the effectors, the described system is able to find the optimal needle position and the depth of the target in a few seconds. FIG. 19 shows a flowchart of this automatic process. FIG. 20 shows the connection and relationship between the different components of the automatic system.

The present invention is however by no means limited to the illlustrative application to needle biopsy. An object of the present invention is to enable the physician to see the targets in 3D and measure their metric distances. The reconstruction need only be done for these targets points and there is no need for expensive volume reconstruction methods such as CT and MRI.

In accordance with the present invention, the choice of the fixed point F is arbitrary, so long as it can be seen within the radiographic images. This fixed point F was called an entry point in the needle biopsy application and could not be chosen arbitrarily in that setting. This was because the aim of physician was to insert the needle at this point into the patient's body and reach the deep seated target for needle biopsy purposes. In the present invention, the fixed point F can be chosen anywhere near the patient's body and such that it be visible in the radiographic images. This is only to define the origin of a 3D coordinate system in which the target points are to be constructed.

An object of the present invention is therefore to facilitate the 3D reconstruction of deep seated target points and the computation of their mutual metric distances. As has been mentioned above, the present invention in this illustrative embodiment utilizes an apparatus and method diclosed in the aforementioned pending patent application in the names of Navab et al.

The 3D reconstruction and metric measurement method is completely non invasive. It enables the physician to chose any arbitrary point as the fixed point F. Since the fixed point is no longer an entry point for needle biopsy, more freedom is provided to the physician in order to chose the fix point F. For example, the fixed point can be chosen near any anatomical organ, even organs that a needle biopsy could not go through.

The present invention then repeats intelligently different steps disclosed in the aforementioned application of Navab et al. in order to find the orientations and the sizes of the vectors $FT^i$ in a coordinate system associated to the positioning device. The points $T^i$ inside the patient body are the points that the physician would like to measure and visualize in 3D.

In the following, these points will be conveniently referred to as target points; however, it must be remembered that these points are not to be considered as targets for a needle biopsy intervention. Naturally, this is not precluded. In the present description, these points are targets in the sense that it is desired to find their 3D position and their mutual metric distances.

The different steps in accordance with the present invention may be summarized as follows, and shown in the flow chart in FIG. 21.

Position the X-ray system such that the deep seated targets $T^1$ are visible on the radiographic image;

position the positioning device at a fix point F visible in the image and close to the patient's body;

adjust the positioning device to an initial configuration defined by $[\Theta=\Theta_1, \phi=0, \alpha=0]$.;

for each target point $T^1$, move the positioning needle around the point F until its image goes through the target image $t^i$; save the positioning parameters $[\Theta=\Theta_1, \phi=\phi^i_1, \alpha=0]$ of the device;

change the positioning device to a new configuration defined by $[\Theta=\Theta_2=\Theta_1, \phi=0, \alpha=0]$;

for each target point $T^1$, move the positioning needle around the point F until its image goes through the target image $t^i$; save the positioning parameters $[\Theta=\Theta_2, \phi=\phi^i_2, \alpha=0]$ of the device; for each target point $T^i$ use $(\phi_1, \phi^i_1, \Theta_2\phi^i_2)$ to compute $\Theta_i'$ and $\alpha_i'$, defining the plane passing thorugh the X-ray source, F and $T^{i}$;

move the X-ray system to a different position for example by rotating it by 90 degrees such that the deep seated targets $T^i$ are visible on the radiographic image;

for each target point $T^i$, change the positioning device to a new configuration defined by $[\Theta=\Theta_i', \phi=0, \alpha=\alpha_i']$;

for each target point $T^i$, move the positioning needle around the point F until its image goes throguh the target image $t^{i}$; save the positioning parameters $[\Theta=\Theta_i', \phi=\phi_i', \alpha=\alpha_i']$; the orientation and the size of all vectors F $T^i$ are now defined; and the points $T^i$ are all reconstructed and their mutual distances $\|FT^i - FT^j\|$ can be computed if necessary.

In accordance with the present invention, the operating physician first selects and identifies the points $t^i$ desired for deriving the metric distances therebetween. This can be done on the fluoroscopic image, utilizing, for example, a computer mouse, a light beam pointer, or any similar device known in the art for performing such selection.

The apparatus is then positioned at an arbitrary point, hereinafter referred to as the fixed point F, near the patient's body. The point F is chosen such that it is visible in the radiographic images taken during the process. For a higher measurement accuracy this point should be chosen as closely as possible to the target points to be reconstructed.

The positioning device, referred to above, then proceeds to Steps I and II for all selected points, as outlined above in connection with depth determination, as follows.

Any plane $\pi_1$ passing through the fixed point F, other than the plane $\pi^i$ which is defined by the entry point F, the target point $T^i$, and the X-ray source position S, intersects the plane $\pi^i$ in one line. This line clearly contains the point F and therefore its image must pass through the image f of the fixed point F on the image on image plane I. The first two steps of the algorithm can now be defined, resulting in a method of accurately obtaining the three dimensional coordinates of the viewing plane $\pi^i$ for each target point $T^i$.

A metallic, or other radiation-opaque bar is rotated around the fixed point F in an arbitrary plane $\pi_1$ passing through the fixed point F. See FIG. 4, which illustrates the step of finding a three-dimensional line lying on the viewing plane $\pi$, similarly $\pi^i$. The shortest distance of the projection line of the three-dimensional line from the target $t^i$ on the image is called $h^i_1$.

This distance $h^i_1$ decreases as the projection of the positioning device needle approaches line $L^i_1$, representing the intersection of the planes $\pi_1$ and $\pi^i$, and vanishes at the intersection of these two planes. This provides a simple way to control the metallic bar under automatic images guidance and move it until it lies on the plane $\pi^i$.

Referring to angles $\Theta$, $\phi$, and $\alpha$ as defined above, an arbitrary plane $\pi$ is selected by fixing angle $\Theta_1$. The appropriate $\phi_1^i$ angles are found for each target point $t^i$ as described in the above paragraph. These are the angles for which the image of the positioning device needle and the target point $t^i$ are aligned.

The positioning device, referred to above, then proceeds to Step II for all selected points, as outlined above in connection with depth determination, as follows.

A metallic (X-ray opaque) bar is rotated around the fixed point F in a second plane $\pi_2$ passing through the fixed point F, and different from $\pi_1$ used in the Step I, see FIG. 5, which illustrates the procedure for finding a second three-dimensional line on the viewing plane $\pi$.

Preferably, the plane passing through F and orthogonal to $\pi_1$ is selected as $\pi_2$. The distance of its projection line from the target $t^i$ on the image, is called $h^i_2$. This distance decreases as the projection line of $\pi_2$ approaches line $L^i_2$, representing the intersection of the planes $\pi^i$ and $\pi_2$ and this distance, $h^i_2$, vanishes at the intersection line of these two planes.

This means that the process is repeated for a second angle $\Theta^2$. Thus, there result two sets of pairs of angles $(\Theta^1, \phi_1^i)$ and $(\Theta^2, \phi_2^i)$, defining i different and distinct viewing planes $\pi^i$.

The radiographic image from a second viewpoint can be obtain by moving the C-arm of the machine arbitrarily; the larger is the angle of rotation the more accurate is the resulting position and orientation of the vectors $FT^i$.

The automatic positioning device next proceeds to Steps III and IV for each target point $t^i$ and computes the 3D position of all the points in the coordinate system associated with the positioning device.

The plane defined by the optical center, the X-ray source S' of the new configuration of the imaging system, the target $T^i$ and the fixed point F is designated as $\pi^{i'}$, analogous to planes $\pi^i$ in the previous determination. See FIG. 6 which shows the procedure for finding the right orientation the vectors $FT^i$.

A metallic bar is rotated around the fixed point F in the plane $\pi^i$ obtained in step II. The distance of its projection line, $l^{i'}$, from the target $t^{i'}$ on the image taken from the new viewpoint, is called $h^{i'}$. This distance decreases as one gets closer to the line $L^{i'}$, representing the intersection of the planes $\pi^i$ and $\pi^{i'}$ and this distance vanishes at the intersection of these two planes.

This provides a way to control the metallic bar manually or automatically using image guidance and move it until the line $FT^i$ is found. $FT^i$ is the line of intersection of the two flat planes $\pi^i$ and $\pi^{i'}$ and it therefore represents a vector direction in space passing through the proposed fixed insertion point F and, when produced, through the target $T^i$. Now, the position of the targets inside the patient body is known to the system in accordance with the invention up to one degree of freedom. Thus the orientation of the line $Ft^i$ from an arbitrary point F to the deep seated target has been computed.

The next step in accordance with the invention, Step IV, is to compute the depth of the target $T^i$ inside the patient from the point F. Once this depth is computed, the deep seated target is fully known, that is, reconstructed, in a known coordinate system attached to positioning device in accordance with the invention.

The cross ratio explained above is used here to accurately compute $FT^i$, the depth of the targets inside the patient's body. Once the depth of the targets $T^i$ from the entry point is computed, as described above, the points are reconstructed in a coordinate system attached to the positioning device and the system can compute their metric distances.

In summary, in order to reconstruct a point seated deep inside the patient's body, the physician positions the positioning device as defined in the aforementioned patent application filed in the name of Navab et al., on the patient body at an arbitrary point F preferably near to the points $T^i$ that the physician wants to reconstruct or do metric distance measurement on. The positioning device finds the planes $\pi^i$ passing through the X-ray source and the line $FT^i$ as described in the step I and II above. The physician is then asked to rotate the C-arm to a new position; the larger is the angle of rotation the more accurate is the resulting orientation of the line $FT^i$.

From this viewpoint the method in accordance with the present invention computes first the orientation of the vector $FT^i$, and then the length of this vector $\|FT^i\|$, through the step III and IV described above. All target points $T^i$ are reconstructed since the point F is known to the device in accordance with the invention and the orientation and the length of all the vectors $FT^i$ are computed in the steps described above. It is therefore possible to compute the distances between all target points $T^i$ and visualize these points in 3D with their correct relative positioning in space. This can in many ways help the physician in planning the intervention, including making sure that the intervention is far enough from some particular anatomical entities during the intervention.

FIG. 22 illustrates an example where three targets T1, T2, and T3 seated inside a body are to be reconstructed. FIG. 23 shows that after the different steps of the method described above the position of the three targets relative to the present positioning device are fully known.

FIG. 24 illustrates how, once the position of the target points relative to the positioning device in accordance with the invention are known, the points can be visualized in 3-D, and the physician can observe these points on the computer screen from any viewing point; furthermore, the invention can also provide the physician with the metric distances between all the target points.

It is understood that data acquisition processing, and storage can be performed by a computer.

While the present invention has been described by way of exemplary embodiments, it will be understood by one of skill in the art that various changes and susbstitutions may be made without departing from the spirit of the invention which is defined by the claims following.

I claim:

1. A method for point reconstruction and metric measurement on radiographic images comprising the following steps:
   a) positioning a fluoroscope for producing a radiographic image, in a position where an operator can observe points inside a patient's body on which points at least one of: (A) reconstruction and (B) metric measurement are to be carried out;
   b) positioning a positioning device on said patient's body at an arbitrarily selected point F visible in a radiographic image;
   c) designating target points $T^i$, being points to be reconstructed by said operator on said radiographic image;
   d) finding planes $\pi^i$ passing through the x-ray source and a line $FT^i$ by successively rotating said positioning device for each target point $T^i$ in first and second different arbitrary planes passing through said point F so that its image goes through an image of said target point $T^i$;
   e) rotating said fluoroscope to a new position and taking a new radiographic image from this new viewpoint;
   f) designating target points $T^i$, being points to be reconstructed, by said operator on said new radiographic image;
   g) computing first the orientation of vectors $Ft^i$;
   h) computing the length of vectors $\|FT^i\|$;
   i) visualizing points $\{T^i, i=1 \ldots n\}$ in a coordinate system associated to the point F; and
   j) computing distances $\|T^iT^j\|$, $i,j=1 \ldots n$.

2. A method for point reconstruction and metric measurement on radiographic images as recited in claim 1 wherein said step c) of designating target points $T^i$ is performed on said radiographic image by using a mouse coordinate translator.

3. A method for point reconstruction and metric measurement on radiographic images as recited in claim 1 wherein said step c) of designating target points $T^i$ is performed on said radiographic image by using a graphics tablet.

4. A method for point reconstruction and metric measurement on radiographic images in an X-ray system including an X-ray source, comprising the following steps:
   a) positioning said X-ray system such that deep seated targets $T^i$ are visible on a fluoroscopy image;
   b) positioning a positioning device at an arbitrary point F close to a patient's body and so as to be visible in said last-mentioned fluoroscopy image;
   c) designating target points $T^i$, being points to be reconstructed, by an operator, on this last-mentioned fluoroscopy image;
   d) adjusting said positioning device to an initial configuration defined by $[\theta=\theta_1, \phi=0, \alpha=0]$;
   e) for each target point $T^i$, moving said positioning device around said point F until its image goes through a target image $t^i$;
   f) saving positioning parameters $[\theta=\theta_1, \phi=\phi i_1, \alpha=0]$ of said positioning device;
   g) changing said positioning device to a new configuration defined by $[\theta=\theta_2=\theta_1, \phi=0, \alpha=0]$;
   h) for each target point $T^i$, moving said positioning device around said point F until its image goes through said target image $t^i$;
   i) saving positioning parameters $[\theta=\theta_2, \phi=\phi i_2, \alpha 0]$ of said positioning device;
   j) for each target point $T^i$ using $(\theta_1, \phi i_1, \theta_2, \phi i_2)$ to compute $\theta_i'$ and $\alpha_i'$, defining a plane passing through said X-ray source, F, and $T^i$;
   k) moving said X-ray system to a different position, such that said deep seated targets $T^i$ are visible on said radiographic image;
   l) for each target point, $T^i$ moving said positioning device around said point F until its image goes through said target image $t^i$;
   m) saving positioning parameters $[\theta=\theta_i', \phi=\phi_i', \alpha=\alpha_i']$ of said positioning device; and
   n) computing the depth of the target.

5. A method for point reconstruction and metric measurement on radiographic images as recited in claim 4 wherein said step c) of designating target points $T^i$ is performed on said radiographic image by using a mouse coordinate translator.

6. A method for point reconstruction and metric measurement on radiographic images as recited in claim 4 wherein said step c) of designating target points $T^i$ is performed on said radiographic image by using a graphics tablet.

7. A method for point reconstruction and metric measurement on radiographic images in an X-ray system, comprising the following steps:
   positioning said X-ray system such that deep seated targets $T^i$ are visible on a radiographic image;

positioning a positioning device at a fixed point F visible in said image and close to a patient's body;

adjusting said positioning device to an initial configuration defined by $[\Theta=\Theta_i, \phi=0, \alpha=0]$;

for each target point $T^i$, moving said positioning device around said point F until its image goes through a target image $t^i$; saving positioning parameters $[\Theta=\Theta_1, \phi=\phi^i_1, \alpha=0]$ of said positioning device;

changing said positioning device to a new configuration defined by $[\Theta=\Theta_2=\Theta_1, \phi=0, \alpha=0]$;

for each target point $T^i$, moving said positioning device around said point F until its image goes through said target image $t^i$;

saving positioning parameters $[\Theta=\Theta_2, \phi=\phi^i_2, \alpha=0]$ of said positioning device;

for each target point $T^i$ using $(\phi_1, \phi^i_1, \Theta_2, \phi^i_2)$ to compute $\Theta_i'$ and $\alpha_i'$, defining a plane passing through said X-ray source, F and $T^i$; moving said X-ray system to a different position such that said deep seated targets $T^i$ are visible on said radiographic image; for each target point $T^i$, changing said positioning device to a new configuration defined by $[\Theta=\Theta_i', \phi=0, \alpha=\alpha_i']$;

for each target point $T^i$, moving said positioning device around the point F until its image goes through the target image $t^{i}$; and saving t positioning parameters.

8. A method for point reconstruction and metric measurement on radiographic images as recited in claim 7 wherein said step of moving said X-ray system to a different position such that said deep seated targets $T^i$ are visible on said radiographic image comprises rotating said X-ray system by 90 degrees.

9. An apparatus for point reconstruction and metric measurement on radiographic images in an X-ray system including an X-ray source, comprising:

a) means for positioning a fluoroscope for producing a radiographic image, in a position where an operator can observe points inside a patient's body on which points at least one of: (A) reconstruction and (B) metric measurement are to be carried out;

b) means for positioning a positioning device on said patient's body at an arbitrarily selected point F visible in a radiographic image;

c) means for designating target points $T^i$, being points to be reconstructed, by said operator on said radiographic image;

d) means for finding planes $\pi^i$ passing through the x-ray source and a line $FT^i$ by successively rotating said positioning device for each target point $T^i$ in first and second different arbitray planes passing through said point F so that its image goes through an image of said target point $T^i$;

e) means for rotating said fluoroscope to a new position and taking a new radiographic image from this new viewpoint;

f) means for designating target points $T^i$, being points to be reconstructed, by said operator on said new radiographic image;

g) means for computing the orientation of vectors $Ft^i$;

h) means for computing the length of vectors $\|FT^i\|$;

i) means for visualizing points $\{T^i, i=1 \ldots n\}$ in a coordinate system associated to the point F; and j) means for computing distances $\|T^iT^j\|$, $i,j=1 \ldots n$.

10. Apparatus for point reconstruction and metric measurement on radiographic images as recited in claim 9 wherein said means for designating target points $T^i$ comprises a mouse coordinate translator.

11. Apparatus for point reconstruction and metric measurement on radiographic images as recited in claim 9 wherein said means for designating target points $T^i$ comprises a graphics tablet.

12. Apparatus for point reconstruction and metric measurement on radiographic images in an X-ray system including an X-ray source, comprising:

a) means for positioning said X-ray system such that deep seated targets $T^i$ are visible on a fluoroscopy image;

b) means for positioning a positioning device at an arbitrary point F close to a patient's body and so as to be visible in said last-mentioned fluoroscopy image;

c) means for designating target points $T^i$, being points to be reconstructed, by an operator, on this last-mentioned fluoroscopy image;

d) means for adjusting said positioning device to an initial configuration defined by $[\theta=\theta_1, \phi=0, \alpha=0]$;

e) for each target point $T^i$, means for moving said positioning device around said point F until its image goes through said target image $t^i$;

f) means for saving positioning parameters $[\theta=\theta_1, \phi=\phi i_1, \alpha=0]$ of said positioning device;

g) means for changing said positioning device to a new configuration defined by $[\theta=\theta_2=\theta_1, \phi=0, \alpha=0]$;

h) means for each target point $T^i$, moving said positioning device around said point F until its image goes through said target image $t^i$;

i) means for saving positioning parameters $[\theta=\theta_2, \phi=\phi i_2, \alpha=0]$ of said positioning device;

j) means for computing for each target point $T^i$ using $(\theta_1, \phi i_1, \theta_2, \phi i_2)$ the quantity $\theta_i'$ and $\alpha_i'$, defining a plane passing through said X-ray source, F, and $T^i$;

k) means for moving said X-ray system to a different position, such that said deep seated targets $T^i$ are visible on said radiographic image;

l) means for moving, for each target point, $T^i$, said positioning device around said point F until its image goes through said target image $t^i$;

m) means for saving positioning parameters $[\theta=\theta_i', \phi=\phi_i', \alpha=\alpha_i']$ of said pointing device; and n) means for computing the depth of the target.

13. Apparatus for point reconstruction and metric measurement on radiographic images as recited in claim 12 wherein said means for designating target points $T^i$ comprises a mouse coordinate translator.

14. Apparatus for point reconstruction and metric measurement on radiographic images as recited in claim 12 wherein said means for designating target points $T^i$ comprises a graphics tablet.

15. Apparatus for point reconstruction and metric measurement on radiographic images as recited in claim 12 wherein said means for designating target points $T^i$ on said radiographic image comprises a mouse coordinate translator.

16. Apparatus for point reconstruction and metric measurement on radiographic images in an X-ray system, comprising:

means for positioning said X-ray system such that deep seated targets $T^i$ are visible on a radiographic image;

means for positioning a positioning device at a fixed point F visible in said image and close to a patient's body;

means for adjusting said positioning device to an initial configuration defined by $[\Theta=\Theta_1, \phi=0, \alpha=0]$;

means for moving, for each target point $T^i$, said positioning device around said point F until its image goes through a target image $t^i$;

means for saving positioning parameters $[\Theta=\Theta_1, \phi=\phi^i_1, \alpha=0]$ of said device;

means for changing said positioning device to a new configuration defined by $[\Theta=\Theta_2=\Theta_1, \phi=0, \alpha=0]$;

means for moving, for each target point $T^i$, said positioning device around said point F until its image goes through said target image $t^i$;

means for saving positioning parameters $[\Theta=\Theta_2, \phi=\phi^i_2, \alpha=0]$ of said positioning device;

means for computing, for each target point $T^i$ using $(\phi_1, \phi^i_1 \Theta_2, \phi^i_2)$ the quantities $\Theta_i'$ and $\alpha_i'$, defining a plane passing thorugh said X-ray source, F and $T^i$;

means for moving said X-ray system to a different position such that said deep seated targets $T^i$ are visible on said radiographic image;

means for changing, for each target point $T^i$, said positioning device to a new configuration defined by $[\Theta=\Theta_i', \phi=0, \alpha=\alpha_i']$;

means for moving, for each target point $T^i$, said positioning device around the point F until its image goes through the target image $t^i$; and means for saving the positioning parameters.

17. Apparatus for point reconstruction and metric measurement on radiographic images as recited in claim 16 wherein said means for moving said X-ray system to a different position moves it such that said deep seated targets $T^i$ are visible on said radiographic image comprises rotating said X-ray system by 90 degrees.

18. A method for point reconstruction and metric measurement using a device actively guided by visual feedback and, more particularly, point reconstruction and metric measurement on radiographic/fluoroscopic images using an automatic positioning device, known per se, and a minimum user interaction with the screen of a display instrument in order to define at least one of: (A) the points to be reconstructed and (B) the points for which metric distances in space need to be measured, said method comprising the steps of:

positioning a positioning device in accordance with said automatic positioning device, known per se, on the body of a patient at an arbitrary point F, near to points $T^i$ to be reconstructed;

finding by way of said positioning device planes $\pi$ passing through the X-ray source and the line $FT^i$, rotating said X-ray source on a C-arm to a new position;

computing the orientation of a vector $FT^i$, and then the length of said vector $\|Ft^i\|$; and calculating distances between all target points $T^i$ and visualizing said points.

19. A method for point reconstruction and metric measurement using a device actively guided by visual feedback and, more particularly, point reconstruction and metric measurement on radiographic/fluoroscopic images using an automatic positioning device, known per se, and a minimum user interaction with the screen of a display instrument in order to define at least one of (A) the points to be reconstructed and (B) the points for which metric distances in space need to be measured, said method comprising the steps of:

positioning said automatic positioning device, known per se, on the body of a patient at a point F near to points $T^i$ on which metric distance measurements are to be done and visible on said radiographic images;

finding by way of said positioning device planes $\pi$ passing through the X-ray source and the line $FT^i$, rotating said X-ray source on a C-arm to a new position;

computing the orientation of a vector $FT^i$, and then the length of said vector $\|Ft^i\|$; and calculating distances between all target points $T^i$ and visualizing said points.

* * * * *